(12) United States Patent
Neel et al.

(10) Patent No.: US 8,394,328 B2
(45) Date of Patent: Mar. 12, 2013

(54) TEST STRIP CONTAINER WITH INTEGRATED METER HAVING STRIP CODING CAPABILITY

(75) Inventors: Gary T. Neel, Weston, FL (US); Brent E. Modzelewski, Boca Raton, FL (US); Cameron Scott Casterline, Pembroke Pines, FL (US); George R. Rounds, Coconut Creek, FL (US); Allan Javier Caban, Lakeworth, FL (US); Adam Mark Will, Boynton Beach, FL (US); Carlos Oti, Plantation, FL (US)

(73) Assignee: Nipro Diagnostics, Inc., Fort Lauderdale, FL (US)

( * ) Notice: Subject to any disclaimer, the term of this patent is extended or adjusted under 35 U.S.C. 154(b) by 996 days.

(21) Appl. No.: 11/352,209

(22) Filed: Feb. 13, 2006

(65) Prior Publication Data
US 2006/0189895 A1 Aug. 24, 2006

Related U.S. Application Data

(63) Continuation-in-part of application No. 11/254,881, filed on Oct. 21, 2005, which is a continuation-in-part of application No. 10/857,917, filed on Jun. 2, 2004, now Pat. No. 8,147,426, said application No. 11/352,209 is a continuation-in-part of application No. 11/181,778, filed on Jul. 15, 2005.

(60) Provisional application No. 60/533,557, filed on Dec. 31, 2003.

(51) Int. Cl.
G01N 21/00 (2006.01)
G01N 21/75 (2006.01)
G01N 31/22 (2006.01)
G01N 33/52 (2006.01)
G01N 35/00 (2006.01)
G01N 15/06 (2006.01)
G01N 33/00 (2006.01)
G01N 33/48 (2006.01)
G01N 25/08 (2006.01)
B01L 3/00 (2006.01)

(52) U.S. Cl. ............ 422/82.05; 422/401; 422/404; 422/430; 422/68.1; 436/150

(58) Field of Classification Search .................. None
See application file for complete search history.

(56) References Cited

U.S. PATENT DOCUMENTS
2,072,796 A 3/1937 Christopher
3,907,503 A 9/1975 Betts et al.
(Continued)

FOREIGN PATENT DOCUMENTS
EP 1 288 653 A1 3/2003
JP 2000/019147 1/2000
(Continued)

*Primary Examiner* — Jill Warden
*Assistant Examiner* — Charles D Hammond
(74) *Attorney, Agent, or Firm* — Finnegan, Henderson, Farabow, Garrett & Dunner LLP

(57) ABSTRACT

A system for diagnostic testing may include a meter for performing a test on a sample applied to a test media and a selectively closable container configured to house test media compatible with the meter. The system may also provide mechanisms for removing a meter from a test container and reattaching it to a new one using one of several coding methods that recalibrate the meter for the new container of test strips. Alternatively, the system may include an auto-calibration system where data is provided individually on each individual test medium in a form readable by the test meter. The carried data may include an embedded code relating to data particular to that individual strip. The data is presented so as to be read by a meter associated with the diagnostic test strip in order to avoid manually inputting the information. In addition, the system may further provide mechanisms to reconfigure the meter to perform a new function when it has been determined that a triggering event has occurred.

33 Claims, 23 Drawing Sheets

U.S. PATENT DOCUMENTS

| | | |
|---|---|---|
| 3,964,871 A | 6/1976 | Hochstrasser |
| 4,059,407 A | 11/1977 | Hochstrasser |
| 4,218,421 A | 8/1980 | Mack et al. |
| 4,615,462 A | 10/1986 | Sacherer et al. |
| 4,627,445 A | 12/1986 | Garcia et al. |
| 4,637,403 A | 1/1987 | Garcia et al. |
| 4,690,801 A | 9/1987 | Anderson |
| 4,717,018 A | 1/1988 | Sacherer et al. |
| 4,757,022 A | 7/1988 | Shults et al. |
| 4,787,398 A | 11/1988 | Garcia et al. |
| 4,797,256 A | 1/1989 | Watlington, IV |
| 4,834,234 A | 5/1989 | Sacherer et al. |
| 4,871,258 A | 10/1989 | Herpichboehm et al. |
| 4,876,068 A | 10/1989 | Castaneda |
| 4,877,580 A | 10/1989 | Aronowitz et al. |
| 4,905,866 A | 3/1990 | Bartell et al. |
| 4,934,556 A | 6/1990 | Kleissendorf |
| 4,995,402 A | 2/1991 | Smith et al. |
| 5,087,556 A | 2/1992 | Ertinghausen |
| 5,096,669 A | 3/1992 | Lauks et al. |
| 5,104,619 A | 4/1992 | de Castro |
| 5,108,889 A | 4/1992 | Smith et al. |
| 5,149,505 A | 9/1992 | English et al. |
| 5,279,294 A | 1/1994 | Anderson et al. |
| 5,281,395 A | 1/1994 | Markart et al. |
| 5,413,764 A | 5/1995 | Haar |
| 5,429,804 A | 7/1995 | Sayles |
| 5,464,118 A | 11/1995 | Grau et al. |
| D367,109 S | 2/1996 | Ryner et al. |
| 5,489,414 A | 2/1996 | Schreiber et al. |
| 5,510,266 A | 4/1996 | Bonner et al. |
| 5,575,403 A | 11/1996 | Charlton et al. |
| 5,589,045 A | 12/1996 | Hyodo |
| 5,628,890 A * | 5/1997 | Carter et al. ............ 204/403.05 |
| 5,630,986 A | 5/1997 | Charlton et al. |
| 5,639,424 A | 6/1997 | Rausnitz |
| 5,645,798 A | 7/1997 | Schreiber et al. |
| 5,649,642 A | 7/1997 | Mabry et al. |
| 5,695,623 A | 12/1997 | Michel et al. |
| 5,709,838 A | 1/1998 | Porter et al. |
| 5,728,352 A | 3/1998 | Poto et al. |
| 5,736,103 A | 4/1998 | Pugh |
| 5,738,244 A | 4/1998 | Charlton et al. |
| 5,791,514 A | 8/1998 | Kirk, III et al. |
| 5,795,543 A | 8/1998 | Poto et al. |
| 5,810,199 A | 9/1998 | Charlton et al. |
| 5,821,399 A | 10/1998 | Zelin |
| 5,854,074 A | 12/1998 | Charlton et al. |
| 5,856,195 A * | 1/1999 | Charlton et al. ............... 436/50 |
| 5,872,713 A | 2/1999 | Douglas et al. |
| 5,904,898 A | 5/1999 | Markart |
| 5,950,865 A | 9/1999 | Menes |
| 5,951,492 A | 9/1999 | Douglas et al. |
| 5,989,917 A | 11/1999 | McAleer et al. |
| 6,036,924 A | 3/2000 | Simons et al. |
| 6,099,484 A | 8/2000 | Douglas et al. |
| 6,106,780 A | 8/2000 | Douglas et al. |
| 6,135,314 A | 10/2000 | Menes |
| 6,159,424 A * | 12/2000 | Kauhaniemi et al. ........... 422/63 |
| 6,168,957 B1 | 1/2001 | Matzinger et al. |
| 6,176,119 B1 | 1/2001 | Kintzig |
| 6,180,063 B1 | 1/2001 | Markart |
| 6,192,891 B1 | 2/2001 | Gravel et al. |
| 6,295,506 B1 | 9/2001 | Heinonen et al. |
| 6,300,142 B1 | 10/2001 | Andrewes et al. |
| 6,315,738 B1 | 11/2001 | Nishikawa et al. |
| 6,319,209 B1 | 11/2001 | Kriz |
| 6,352,514 B1 | 3/2002 | Douglas |
| 6,379,317 B1 * | 4/2002 | Kintzig et al. ................ 600/573 |
| 6,540,675 B2 | 4/2003 | Aceti et al. |
| 6,544,475 B1 | 4/2003 | Douglas et al. |
| 6,558,897 B2 | 5/2003 | Scheuringer |
| 6,581,799 B1 | 6/2003 | Garrant et al. |
| 6,612,461 B2 | 9/2003 | Layer et al. |
| 6,623,698 B2 | 9/2003 | Kuo |
| 6,669,908 B2 | 12/2003 | Weyker et al. |
| 6,682,704 B2 | 1/2004 | Bottwein et al. |
| D487,594 S | 3/2004 | Alscher et al. |
| 6,743,635 B2 * | 6/2004 | Neel et al. ........................ 436/95 |
| 6,770,487 B2 | 8/2004 | Crosby |
| 6,814,844 B2 * | 11/2004 | Bhullar et al. ........... 204/403.01 |
| 6,997,344 B2 * | 2/2006 | Brown et al. .................. 221/258 |
| 7,092,891 B2 * | 8/2006 | Maus et al. ........................ 705/2 |
| 7,138,089 B2 * | 11/2006 | Aitken et al. ............... 422/82.01 |
| 7,998,407 B2 * | 8/2011 | Wohland ...................... 422/404 |
| 2002/0057993 A1 | 5/2002 | Maisey et al. |
| 2002/0060247 A1 * | 5/2002 | Krishnaswamy et al. ......................... 235/472.01 |
| 2002/0150501 A1 | 10/2002 | Robertson et al. |
| 2002/0188224 A1 | 12/2002 | Roe et al. |
| 2003/0031591 A1 | 2/2003 | Whitson et al. |
| 2003/0031595 A1 | 2/2003 | Kirchhevel et al. |
| 2003/0032190 A1 | 2/2003 | Brown et al. |
| 2003/0036200 A1 | 2/2003 | Charlton |
| 2003/0059350 A1 | 3/2003 | Sacherer |
| 2003/0109777 A1 | 6/2003 | Kloepfer et al. |
| 2003/0111357 A1 | 6/2003 | Black |
| 2003/0129088 A1 | 7/2003 | Lee et al. |
| 2003/0133847 A1 | 7/2003 | Hagen et al. |
| 2003/0161762 A1 | 8/2003 | Caron et al. |
| 2003/0175155 A1 | 9/2003 | Charlton |
| 2003/0185705 A1 | 10/2003 | Otake |
| 2003/0185708 A1 | 10/2003 | Otake |
| 2003/0186446 A1 | 10/2003 | Pugh |
| 2003/0191415 A1 | 10/2003 | Moerman et al. |
| 2003/0207454 A1 | 11/2003 | Eyster et al. |
| 2003/0208140 A1 | 11/2003 | Pugh |
| 2003/0211625 A1 | 11/2003 | Cohen et al. |
| 2003/0212345 A1 | 11/2003 | McAllister et al. |
| 2003/0219357 A1 | 11/2003 | Douglas et al. |
| 2003/0223906 A1 | 12/2003 | McAllister et al. |
| 2004/0007585 A1 | 1/2004 | Griffith et al. |
| 2004/0047764 A1 | 3/2004 | Purcell |
| 2004/0048394 A1 | 3/2004 | Kirchhevel |
| 2004/0244151 A1 | 12/2004 | Sakata et al. |
| 2005/0009126 A1 | 1/2005 | Andrews et al. |
| 2005/0019953 A1 | 1/2005 | Groll |
| 2005/0143675 A1 | 6/2005 | Neel et al. |
| 2010/0004522 A1 * | 1/2010 | Varela .......................... 600/347 |

FOREIGN PATENT DOCUMENTS

| | | |
|---|---|---|
| WO | WO 94/10558 * | 5/1994 |
| WO | WO 96/13707 | 5/1996 |
| WO | WO 97/29847 | 8/1997 |
| WO | WO 99/59657 | 11/1999 |
| WO | WO 01/23885 | 4/2001 |
| WO | WO 03/082091 | 10/2003 |
| WO | WO 2005/102154 | 11/2005 |

* cited by examiner

TEST STRIP CONTAINER WITH INTEGRATED METER HAVING STRIP CODING CAPABILITY

CROSS-REFERENCE TO RELATED APPLICATIONS

This application is a continuation in part of U.S. application Ser. No. 11/254,881, filed Oct. 21, 2005, which is a continuation in part of U.S. application Ser. No. 10/857,917, filed Jun. 2, 2004 now U.S. Pat. No. 8,147,426, which claims the benefit of Provisional U.S. Patent Application 60/533,557, filed Dec. 31, 2003, all of which are incorporated herein by reference in their entirety. This application is also a continuation in part of U.S. application Ser. No. 11/181,778, filed Jul. 15, 2005, which is also incorporated herein by reference in its entirety.

In addition, this application is related to U.S. application Ser. No. 11/144,715, filed Jul. 6, 2005, as well as U.S. Design Pat. No. D506,832, issued Jun. 28, 2005, and U.S. Pat. No. D507,657, issued Jul. 19, 2005, both entitled "METER FOR AN INTEGRATED DIAGNOSTIC TEST SYSTEM," all of which are incorporated herein by reference in their entirety.

FIELD OF THE INVENTION

The present invention relates to the field of diagnostic testing and, more particularly, to diagnostic testing systems using electronic meters.

BACKGROUND OF THE INVENTION

Diagnostic testing systems are commonly used to perform various types of diagnostic tests on various types of samples. The diagnostic test may be a qualitative or quantitative test to determine the presence, concentration or amount of one or more analytes in a sample. The analyte may be a medically significant analyte—e.g., glucose, ketones, cholesterol, triglycerides, human choriogonadotropin (HCG), hemoglobin A1C, fructosamine, carbohydrates, tumor markers, lead, anti-epilepsy drugs, bilirubin, liver function markers, toxins or their metabolites, controlled substances, blood coagulation factors (PT, APTT), etc.—contained in a biological sample—e.g., blood, urine, tissue, saliva, etc. However the diagnostic test is not limited to the medical field. For instance, the diagnostic test may determine the presence or quantity of an analyte in a water, soil or chemical sample.

Such diagnostic testing systems may include a test media (e.g., a test strip, tab, disc, etc.) configured to react to the presence of the analyte in a sample, and a separate electronic meter configured to interface with the test media in order to conduct the diagnostic test and indicate the results of the diagnostic test to the user.

In order to conduct the diagnostic test, a user must first obtain a sample test media, e.g., a test strip, from a container, then obtain a sample using a sampling device (e.g., by drawing blood using a lancet), and then apply the sample to the test media (either before or after inserting the test media into the meter interface). The meter then performs the diagnostic test on the sample and indicates the result to the user, e.g., using a numerical display.

However, the diagnostic meter is often bulky. Further, because the user must pick up and put down the test media container, sampling device and meter in succession, the test media container, sampling device and meter are easily separated from each other, so that users may find themselves without one or more of the components necessary to conduct the diagnostic test. Further, it is inconvenient for the user to carry a separate test media container, electronic meter and sampling device.

Further, test media from different brands or manufacturing lots may respond differently to the presence or concentration of analyte in the sample. In order to obtain more accurate results, the electronic meter may be calibrated with respect to a given brand or lot of test strips by providing it with one or more brand- or lot-specific calibration parameters that correlate the response from particular a particular brand or lot of test media to a standardized reference.

The user may be required to provide the meter with the appropriate calibration parameters in a separate "coding" step. For example, the test media container may display a code number from which the meter can determine the appropriate calibration information. The user may then manually enter the code number (e.g., using buttons or other user input devices on the meter) so as to provide the calibration data to the meter. Alternatively, the calibration data may be downloaded, e.g., from a manufacturer's website. In another approach, the test media container may be provided with an associated code chip in which the calibration data is stored electronically. The user may provide the calibration data to the meter by inserting the code chip into a corresponding port on the meter.

This coding step can be inconvenient or difficult for the user. For example, elderly or infirm users may have difficulty downloading calibration data or inserting code chips. Further, users may forget to calibrate the meter for use with a new brand or lot of test media. Consequently, the user may enter incorrect calibration parameters or codes, or the user may use test media from one brand or lot with a meter calibrated for use with test media from a different brand or lot. In addition, once a meter is calibrated for a given lot of test media, the use of that meter with test media from another lot may lead to erroneous results that could have serious consequences for the user. For example, where the test is a self-test of blood glucose level, an erroneous result can misinform the user as to their blood glucose level, which may lead to the user having a diabetic seizure.

A possible solution to the above-mentioned coding problems is utilizing the method of universal coding. This method uses strip lots that are controlled and sorted to a narrow acceptance criteria, i.e. all strips are conformed to a single set of calibration parameters, thus not requiring strip coding or more than one fixed set of strip lot parameters to be stored in the meter 130. Universal coding saves the cost of replacing the meter 130 by allowing it to be used on many different test strip containers 110. In addition, universal coded strips 120 can be tightly controlled such that many strip lots have the same code and are sorted to fit the meter's fixed code assignment. This method is not technique dependent and helps prevent errors due to mixed strip lots. Furthermore, universal coding always has the correct code such that there is no miss-match between the meter 130 and the strip lot code. However, the narrow limits imposed by this method make this an expensive solution as large amounts of waste are generated during the current manufacturing processes.

Accordingly, there is a need for diagnostic testing systems that are convenient to carry and that minimize the chance that a user will use a diagnostic meter with test media from a brand or lot for which the meter has not been calibrated. In addition, there is a need for diagnostic testing systems that reduce the potential for testing a sample with a test meter improperly calibrated for the particular test media used.

SUMMARY OF THE INVENTION

Embodiments of the present invention are directed to systems and methods for diagnostic testing that obviate one or more of the limitations and disadvantages of prior systems and methods.

In one embodiment, a system for diagnostic testing includes a meter comprising a housing, an interface for accepting test media in order to perform the diagnostic test, and a controller configured to perform the diagnostic test. The system also includes a container, having an opening, operatively associated with the meter and configured to contain test media compatible with the meter. Test media initially stored in the container and comprising at least one test strip is embedded with a code readable by the controller to identify data particular to the test strip.

Another embodiment of the invention is directed to a system for diagnostic testing including a meter for performing a diagnostic test on a sample applied to test media. The meter comprises a housing, an interface for accepting test media in order to perform the diagnostic test, and a controller configured to perform the diagnostic test. A container has an opening and is operatively associated with the meter and configured to contain test media compatible with the meter. Test media initially stored in the container comprises at least one diagnostic test strip. The test strip comprises at least one electrically insulating layer; a conductive pattern formed on the at least one insulating layer includes at least one electrode disposed on the at least one insulating layer at a proximal region of the strip, electrical strip contacts disposed on at least one insulating layer at a distal region of the strip, and conductive traces electrically connecting the electrodes to at least some of the electrical strip contacts. A reagent layer contacts at least a portion of at least one electrode and each of the electrical strip contacts is selectively coverable with a discrete portion of electrical insulating material to at least partially form a distinct pattern readable by the controller to identify data particular to the test strip.

Another embodiment of the invention is directed to a system for diagnostic testing including a meter for performing a diagnostic test on a sample applied to test media. The meter comprises a housing, an interface for accepting test media in order to perform the diagnostic test, and a controller configured to perform the diagnostic test. A container has an opening and is operatively associated with the meter and configured to contain test media compatible with the meter. Test media initially stored in the container comprises at least one diagnostic test strip. The test strip comprises at least one electrically insulating layer; a conductive pattern formed on the at least one insulating layer includes at least one electrode disposed on the at least one insulating layer at a proximal region of the strip, electrical strip contacts disposed on at least one insulating layer at a distal region of the strip, and conductive traces electrically connecting the electrodes to at least some of the electrical strip contacts. A reagent layer contacts at least a portion of at least one electrode. A first plurality of electrical strip contacts is comprised of contacts individually connected to an electrode. A second plurality of electrical strip contacts is comprised of the conductive pattern at the distal region of the strip and an electrically insulating material separates the first and second plurality of electrical strip contacts.

Another embodiment of the invention is directed to a system for diagnostic testing including a meter comprising a housing, an interface for accepting test media in order to perform the diagnostic test, and a controller configured to perform the diagnostic test. The system also includes a container having an opening and configured to contain test media compatible with the meter. Test media initially stored in the container and comprising at least one test strip is embedded with a code readable by the controller to identify data particular to the test strip. The meter housing is configured to close the container opening.

In another embodiment, the invention is directed to a method of determining a constituent level within a fluid. The method comprises providing a diagnostic test system including a meter comprising a housing, an interface for accepting test media in order to perform the diagnostic test, and a controller configured to perform the diagnostic test. The method further comprises providing a container with an opening configured to contain test media compatible with the meter and providing test media initially stored in the container comprising at least one test strip embedded with a code readable by the controller. The method further comprises removing a test strip from the container; inserting a first end of the strip into the meter interface; applying a fluid sample at a second end of the strip; reading the code embedded on the test strip with the controller; identifying data particular to the test strip based on the code; and calculating the fluid constituent concentration of the fluid sample with the controller.

Additional aspects and advantages of the invention will be set forth in part in the description which follows, and in part will be obvious from the description, or may be learned by practice of the invention. The advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

1. The Integrated System

Figure 1:
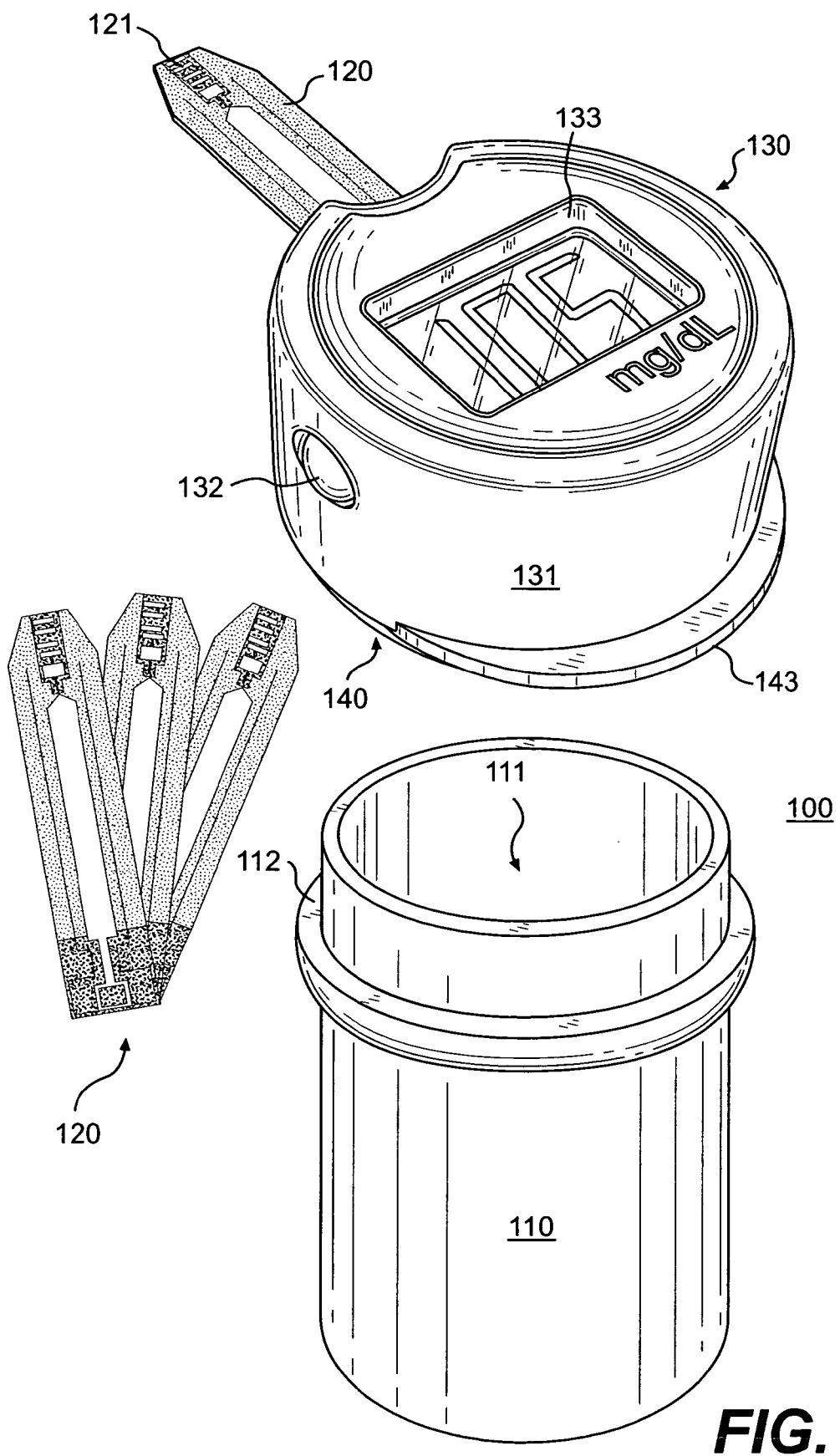
FIG. 1 is a perspective view of a first embodiment of an integrated system consistent with the present invention.

FIG. 1 shows an integrated system 100 for conducting a diagnostic test in accordance with an exemplary embodiment of the present invention. Exemplary integrated system 100 includes a container 110 for containing test media, such as test strips 120, and a meter 130 for performing a diagnostic test using the test strips 120 contained in container 110.

In one illustrative embodiment, the diagnostic test is the determination of the amount of glucose in a sample of whole blood applied to a sample chamber 121 of test strip 120. For blood glucose testing, meter 130 may employ any of a variety of techniques. Preferably, the diagnostic test employs an electrochemical technique (e.g., coulometry, amperometry, potentiometry, etc.). Exemplary electrochemical systems are described in prior U.S. Pat. No. 6,743,635, issued Jun. 1, 2004, and U.S. Pat. No. 6,946,299, issued Sep. 20, 2005, both entitled "SYSTEM AND METHOD FOR BLOOD GLUCOSE TESTING" and both having assignee in common with the instant application, which are incorporated by reference herein in their entirety. Alternatively, meter 130 may employ a photometric technique (e.g., reflection, transmission, scattering, absorption, fluorescence, electro-chemiluminescence, etc.) to determine the amount of glucose in the sample. Exemplary photometric systems are described in U.S. Pat. Nos. 6,201,607, 6,284,550 and 6,541,266, each having assignee in common with the instant application, which are incorporated by reference herein in their entirety. However, electrochemical techniques are currently preferred because, among other reasons, they require a smaller blood sample (on the order of 1 µL or less) than the photometric techniques (on the order of 1 µL or greater). Further, the instrumentation for the electrochemical techniques typically requires less power and can typically be made more compactly than the instrumentation for the photometric techniques.

Integrated system 100 will be illustrated with reference to a diagnostic test to determine the concentration of blood glucose using an electrochemical technique, with the understanding that the principles of the present invention are equally applicable to other types of diagnostic tests and techniques, such as those mentioned above. Further, although the present invention has been illustrated as utilizing test media in the form of test strips 120, exemplary embodiments of the present invention are not limited to a particular type of media and those of skill in the art will recognize that the principles of the present invention are equally applicable to diagnostic testing systems which employ test media in other forms, e.g., tabs, discs, etc.

Figure 6:
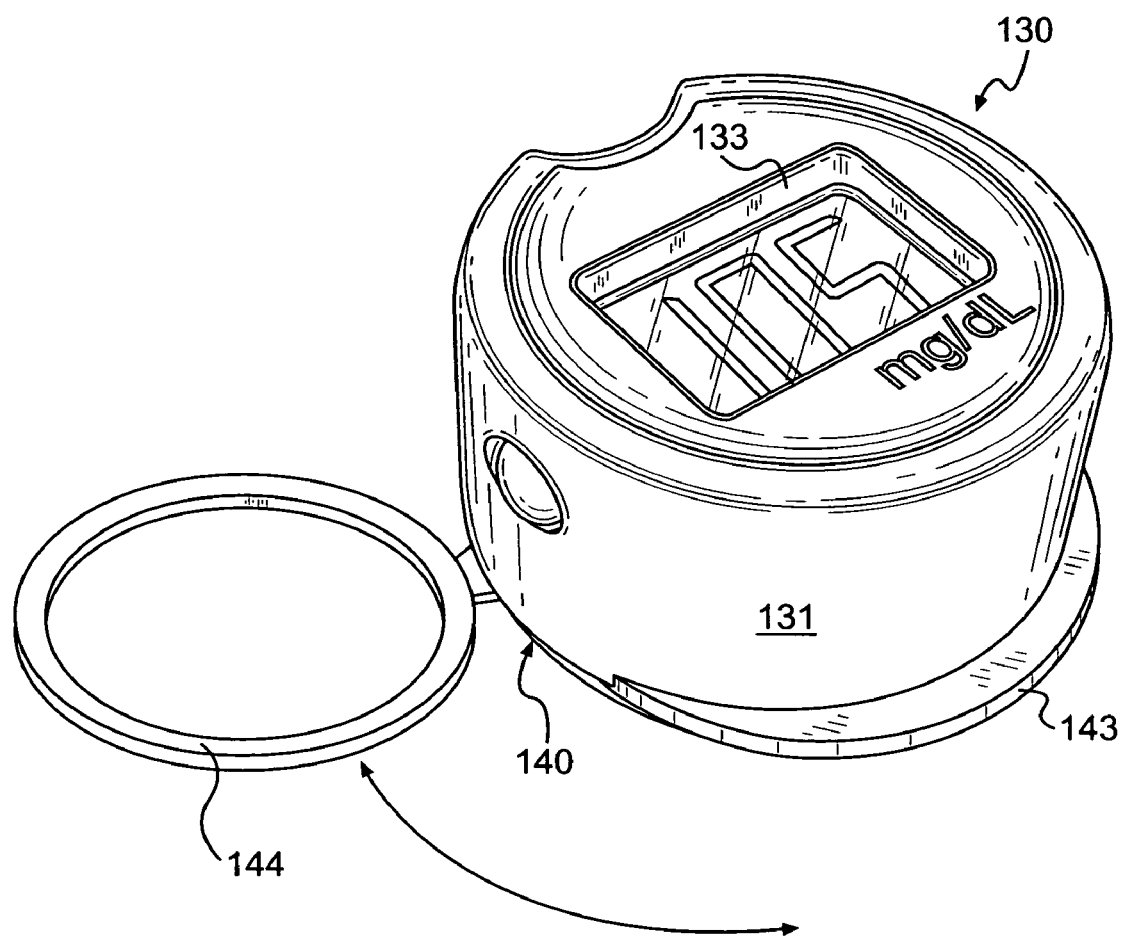
FIG. 6 is a perspective view of a meter housing comprising a holder configured to receive one or more devices used for diagnostic testing.

Meter 130 may be contained within a housing 131. The meter housing 131 is attached to or otherwise includes a closure portion 140 (bottom of meter 130 in FIG. 1) which engages container 110 in order to selectively close an opening 111 of the container. Meter housing 131 may additionally include a holder 144 that is configured to receive one or more containers 110, as illustrated in FIG. 6. Holder 144 is configured to be stored underneath closure 140 when not in use and is slidably movable (as illustrated by the position arrow) to a side position of the container 110 in order to receive and hold additional containers 110. Opening 111 may be the only opening in the container 110. In an illustrative embodiment, meter housing 131 has one side (e.g., the bottom of meter housing 131 in FIG. 1) which is shaped to conform to the closure 140 and is affixed to the closure 140, e.g., by a mechanical attachment (clips, etc.), bonding, gluing, welding, etc. Alternatively, closure portion 140 may be formed integrally with the meter housing 131. The meter 130 and closure 140 together thus form a cap or lid for the container 110.

The closure 140 may be configured to engage the container in a number of ways. In the closed position (see FIG. 3), closure 140 closes opening 111 sufficiently to prevent loss or removal of the test media from container 110. Accordingly, closure 140 is configured to engage container 110 so as to prevent test strips 120 from passing through opening 111 when closure 140 is in the closed position. Container 110 and closure 140 may also be configured to prevent the infiltration of light, liquid, vapor, and/or air into the container so as to prevent contamination or degradation of the test media. Where the test media is configured such that it is toxic or may present a choking hazard, closure 140 may optionally be configured to be child-resistant in order to prevent children from opening container 110 and accessing the test media. For example, closure 140 and container 110 may be configured in a manner similar to well known child-resistant containers for pharmaceuticals or household chemicals.

Figure 2:
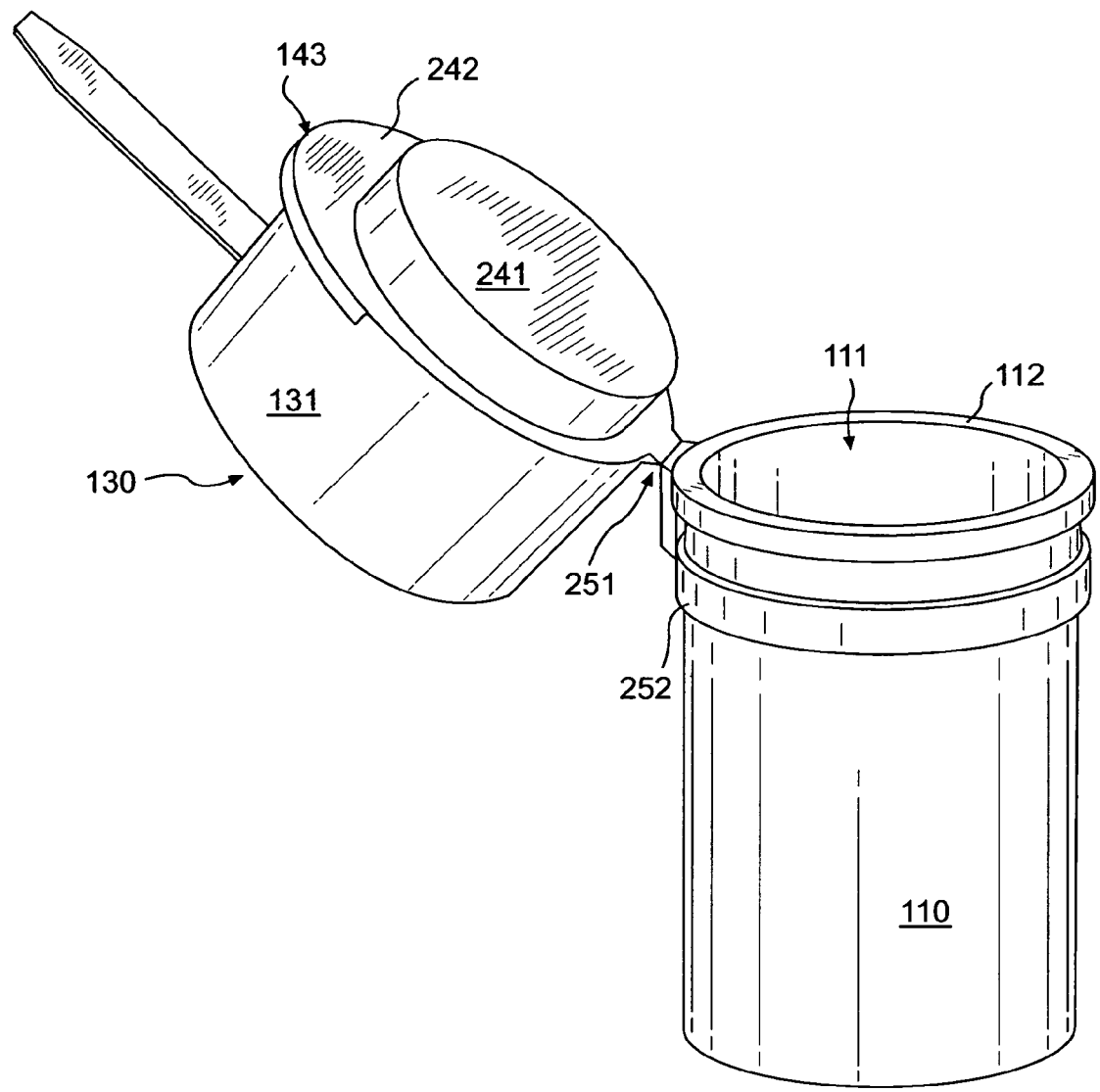
FIG. 2 is a perspective view of a second embodiment of an integrated system consistent with the present invention.

Closure 140 may be configured as a twist-off cap, e.g., by providing inter-engaging threads (not shown) on the closure 140 and the container 110. Alternatively, closure 140 may be configured to slide over the opening, e.g., within grooves (not shown) beside the opening. As a further alternative, closure 140 may be provided with a catch (not shown), such as a detent, that engages container 110 (or vice versa). The catch may be released by a button. However, in an illustrative embodiment, the closure 140 is configured to form a press-fit seal with the container so as to seal the opening against the infiltration of light, liquid and vapor. For example, in FIG. 1, closure 140 is configured with a recess (not shown) to press-fit to the outside of the opening 111, so that the rim of the opening 111 fits within the closure portion 140. Alternatively, closure 140 may be configured with a projection 241 shaped to engage the inside of the opening 111, as shown in FIG. 2. However, it will be understood that the present invention is not limited to any particular configuration of the container and closure and that other configurations may be employed consistent with the principles of the present invention.

For ease of manufacture, opening 111 may be made in the same shape as the container 110. The housing 131 of meter 130 is likewise preferably have an exterior shape similar to that of the container 110 so that the integrated system may be more comfortably held and carried, e.g., in a user's pocket. However, it will be understood that the container 110, meter 130 and opening 111 need not be of the same exterior shape, and the container and meter may be configured in different shapes without departing from the scope of the present invention.

Preferably, the container 110 is generally a right circular cylinder and opening 111 has a circular shape as shown in FIGS. 1 and 2. A circular shape is one possible configuration for the opening because it allows a uniformly tight seal to be formed with a press-fit between the closure portion 140 and the container 110. As shows in FIGS. 1-3, meter 130 may also be generally circular and cylindrical and have a width similar to the width of the container so that the integrated meter 100 has an overall generally circular-cylindrical shape that is comfortable to hold and to carry, e.g., in a pants pocket. However, the container 110, meter 130 and opening 111 may be made in any of a number of other shapes. For example, the container may formed as a right oval, elliptical or rectangular cylinder in order to better conform to a user's shirt pocket.

Figure 3:
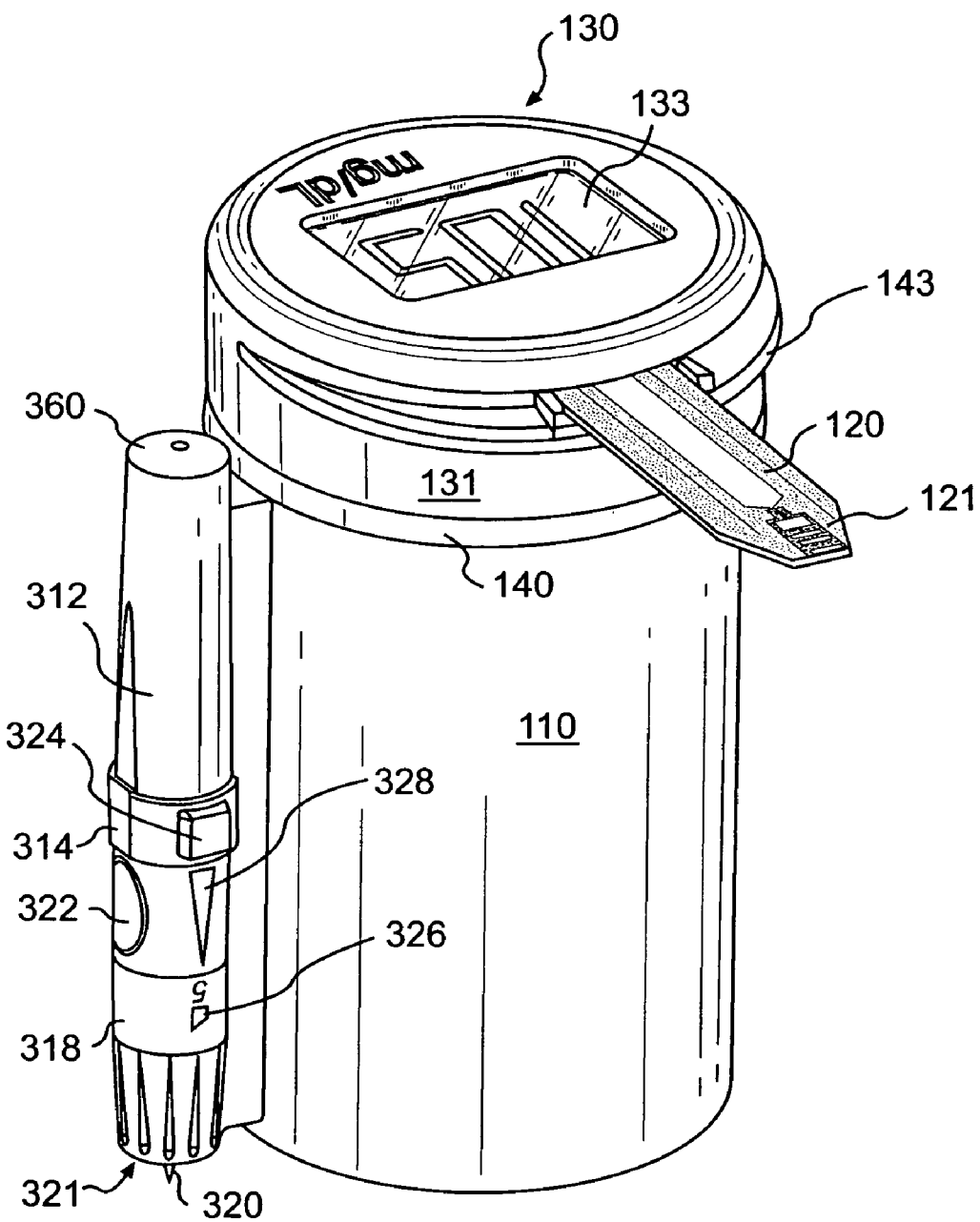
FIG. 3 is a perspective view of a third embodiment of an integrated system consistent with the present invention.

Container 110 and closure 140 may also be provided with corresponding flanges 112 and 242, respectively, that fit flush against each other when the closure portion is in the closed position in order to further prevent the infiltration of liquid and vapor. Closure 140 is also preferably provided with a protrusion 143 which extends beyond the side of container 110 sufficiently to aid to the user in opening and closing the container 110, e.g., by pushing upward with the thumb against the protrusion 143. Protrusion 143 may be an extension of the flange 242, as shown in FIG. 2. Alternatively, protrusion 143 may be formed directly on meter housing 131, as shown in FIG. 3.

Figure 7:
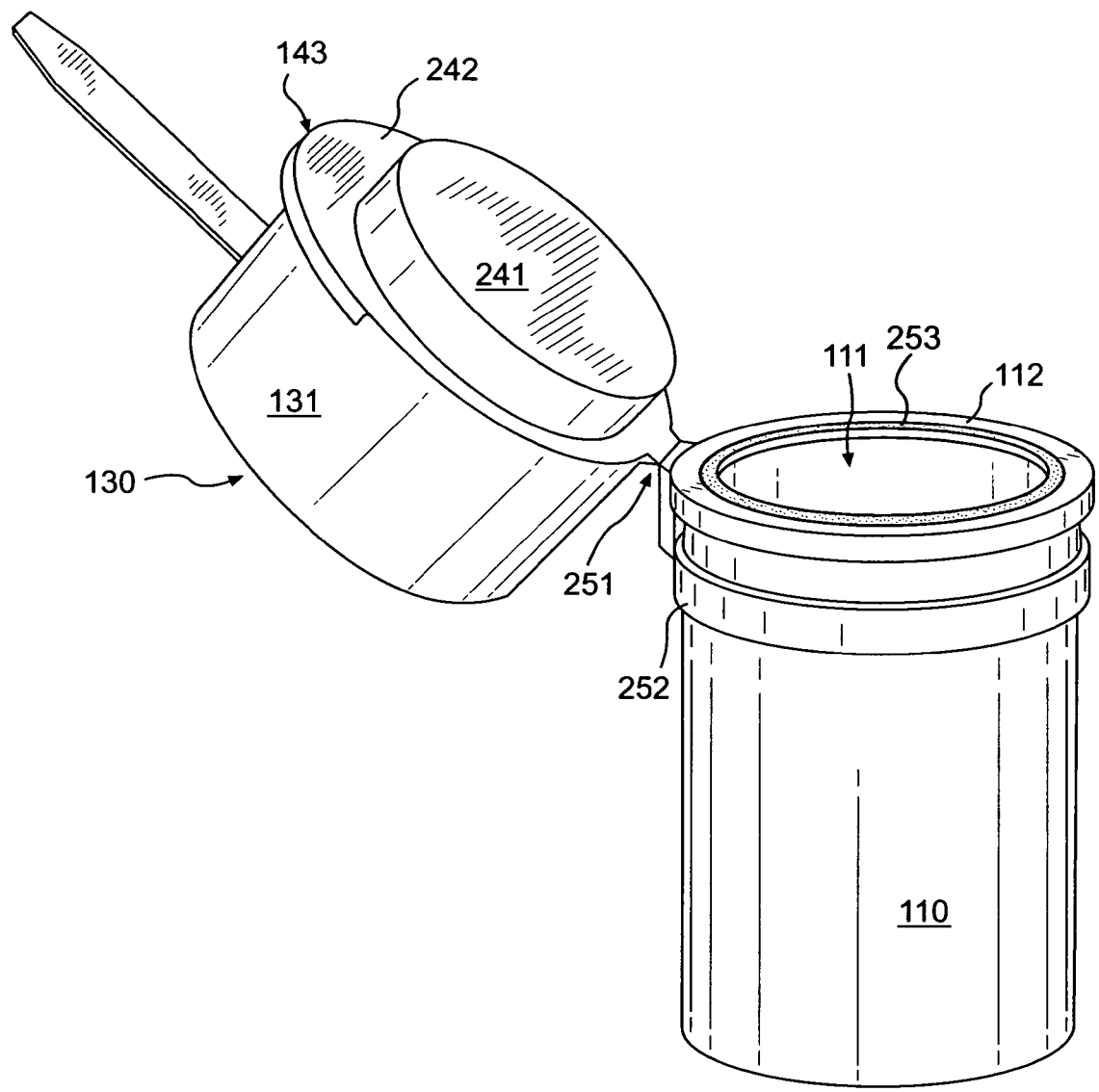
FIG. 7 is a perspective view of a container with a light emitting diode located on the container.
Figure 8:
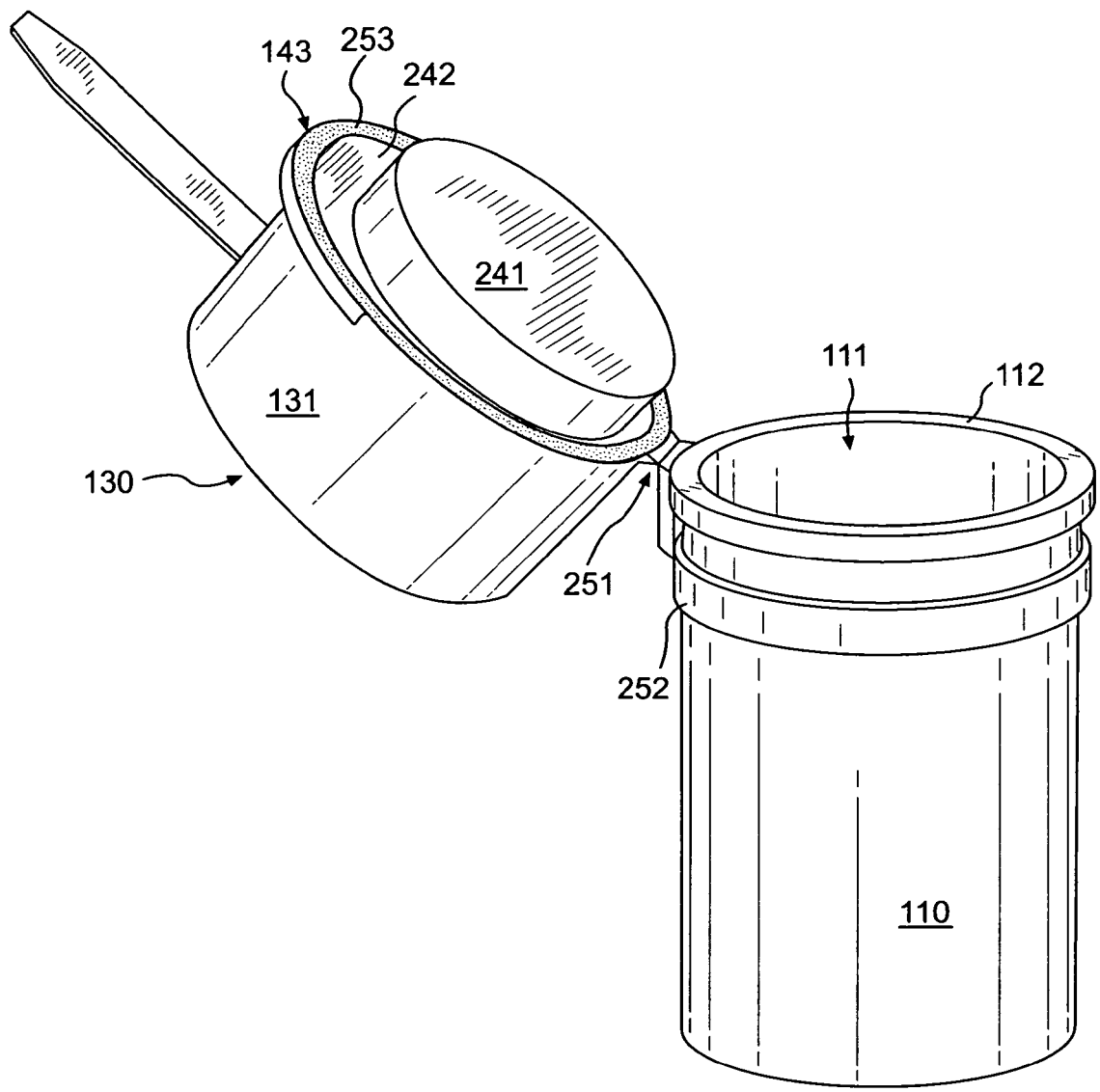
FIG. 8 is a perspective view of a container with a light emitting diode located on the meter.
Figure 9:
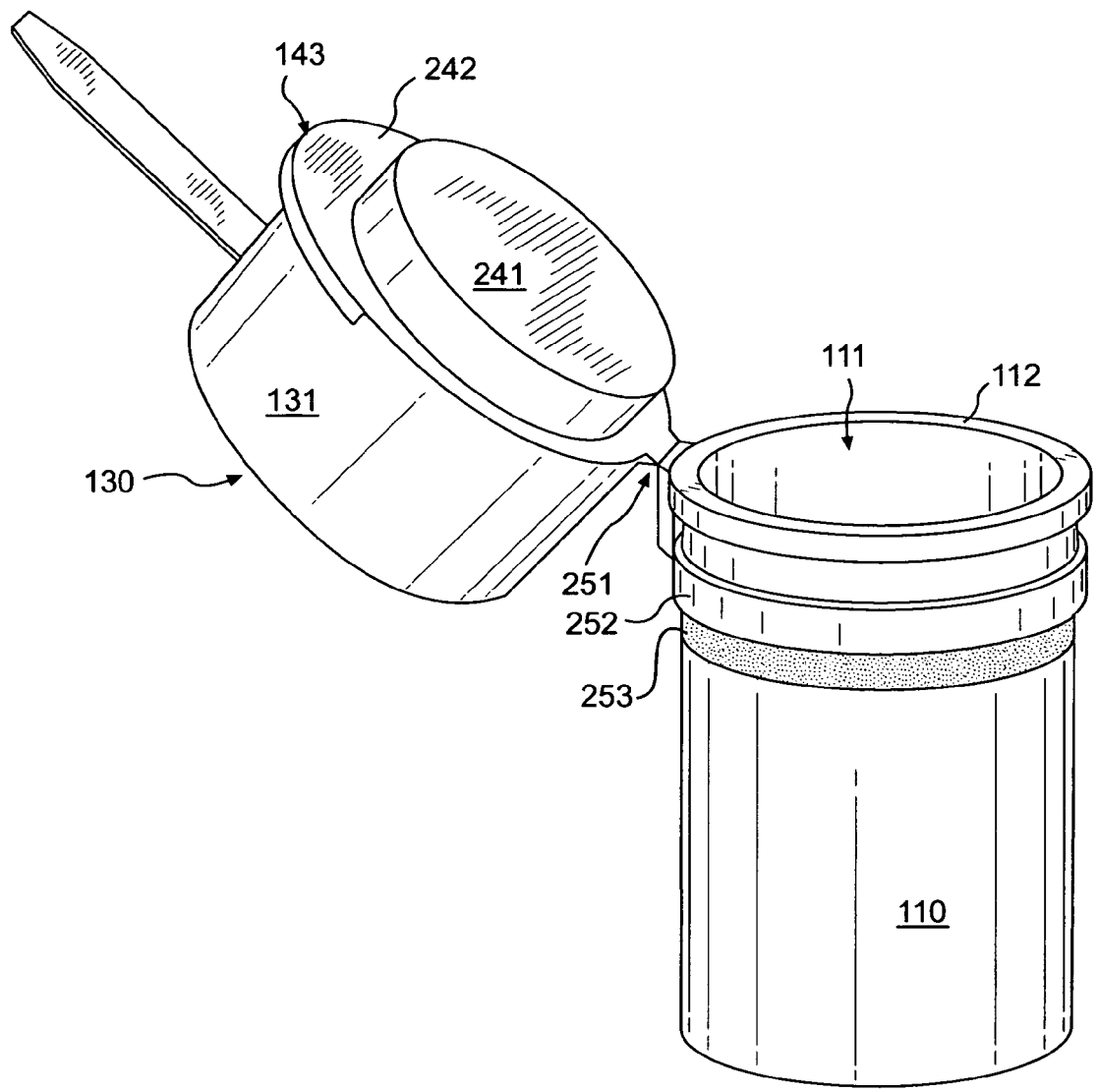
FIG. 9 is a perspective view of a container with a light emitting diode positioned additionally to illuminate an exterior portion of the container.
Figure 10:
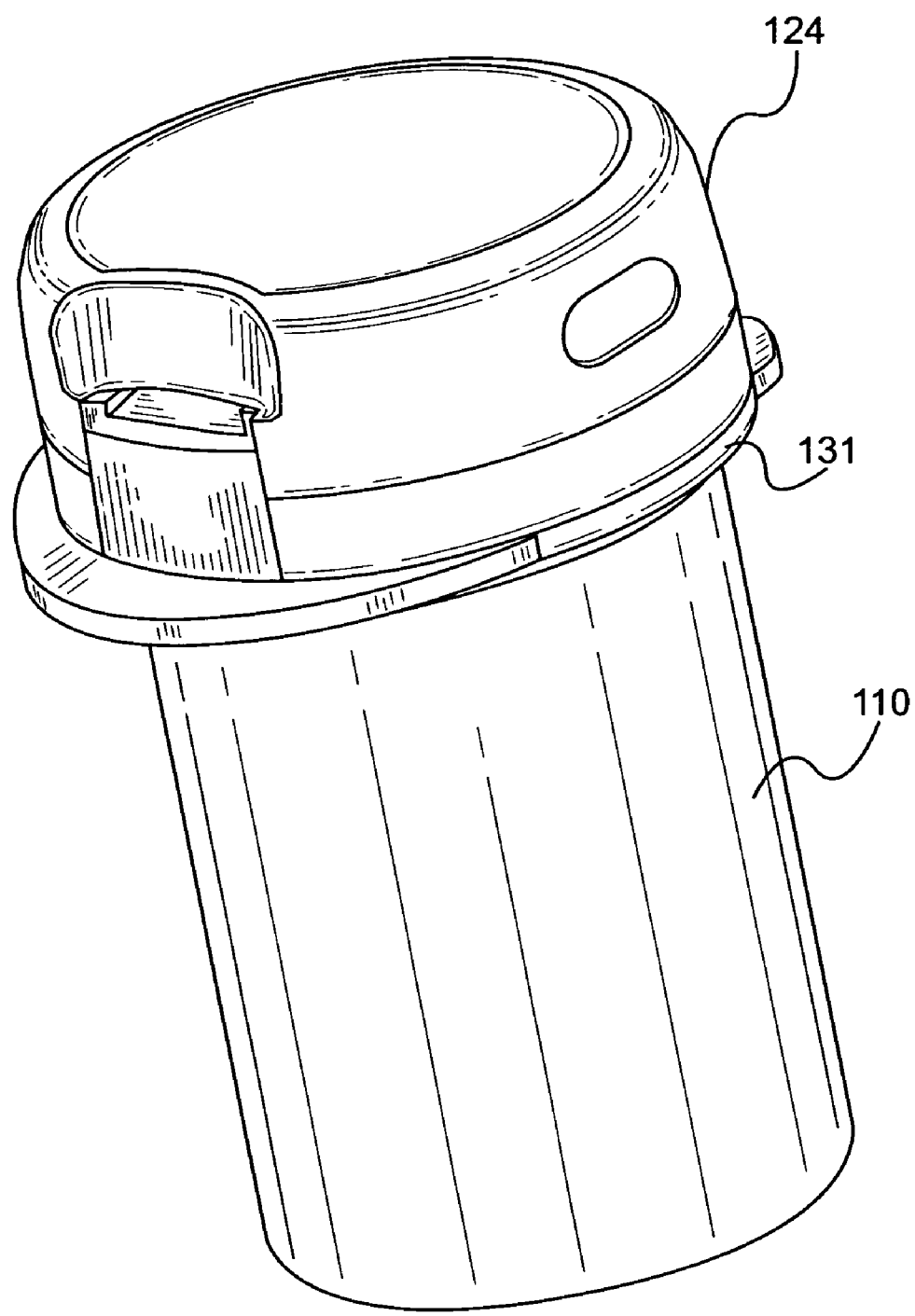
FIG. 10 is a perspective view of a closed container with an illuminated housing.
Figure 11:
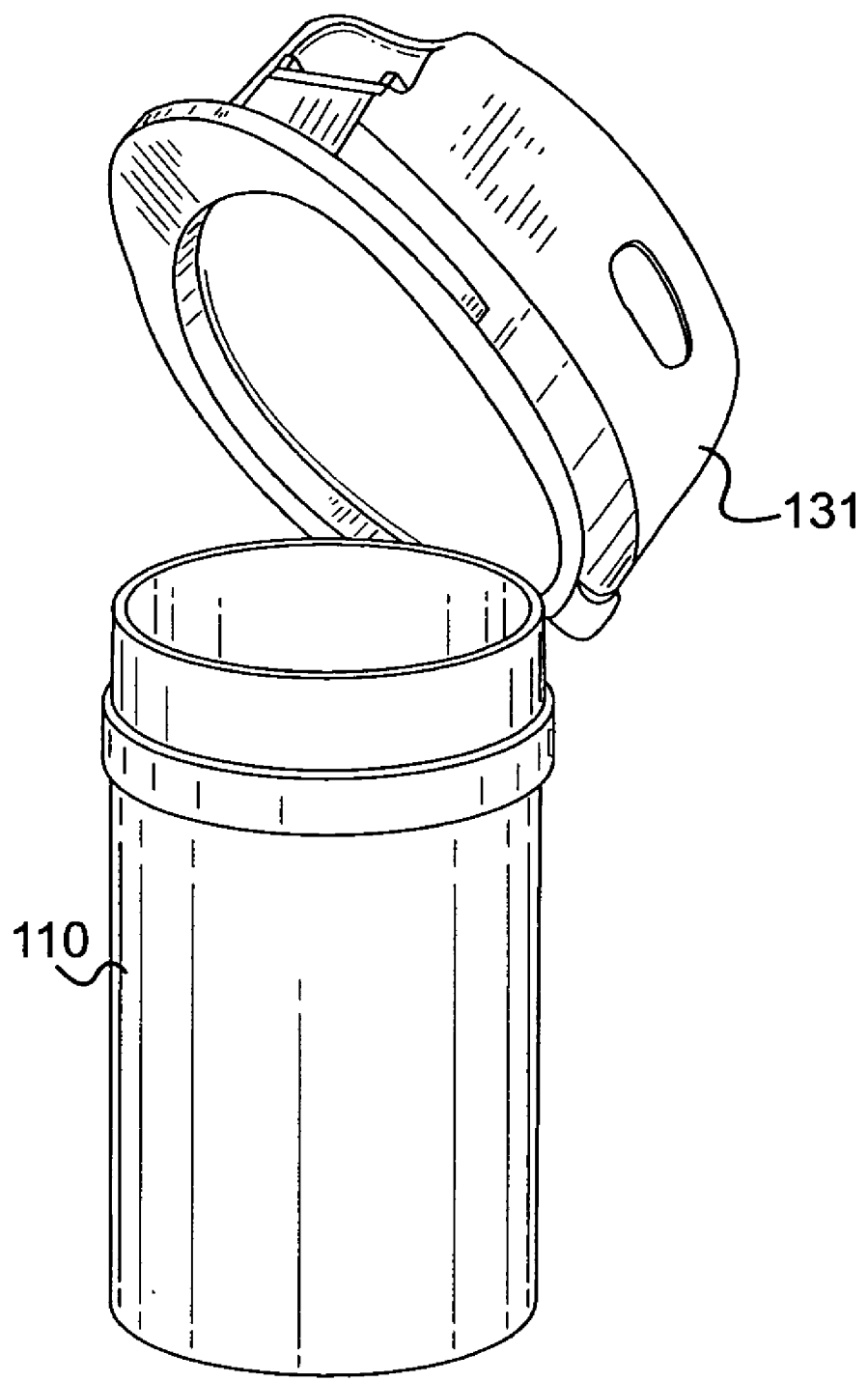
FIG. 11 is a perspective view of an open container with an illuminated housing.

As shown in FIG. 1, container 110 may be opened by completely removing meter 130 and closure portion 140 from the container 110. Alternatively, meter 130 and/or closure 140 may be connected to container 110 in order to prevent the meter 130 from becoming separated from the container. Container 110 and meter 130 may be connected by, e.g., a hinge, lanyard or other flexible connector, such as a flexible plastic band or wire, etc. (not shown). In an illustrative embodiment, a hinge 251 connects the container 110 and the meter housing 131 and/or closure 140. Hinge 251 is positioned such that projection 241 fits within opening 111 in the closed position. The connector (e.g., hinge 251) may have one end connected to the container 110 and the other end connected to the closure 140 and/or meter housing 131. For example, container 110 and closure 140 may be integrally connected by a hinge, e.g., as shown in U.S. Pat. No. 5,723,085, entitled "PROCESS AND APPARATUS FOR MAKING A LEAK PROOF CAP AND BODY ASSEMBLY," which is incorporated by reference herein in its entirety. Alternatively, one end of the connector (e.g., hinge 251) may be connected to a ring 252 that is sized to fit over container 110, as shown in FIG. 2. Ring 252 may be configured to loosely frictionally engage container 110. As another alternative, ring 252 may be affixed to the container 110, e.g., by welding, gluing, etc. In addition, the container 110 may include a light emitting diode (LED) 253 that automatically or selectively illuminates the contents of the container 110 when it is opened. The LED 253 may positioned on the container 110, on the meter housing 131, or positioned additionally to illuminate an exterior portion of the container 110, as illustrated in FIGS. 7-9.

In an exemplary embodiment, container 110 and closure 140 are formed of polypropylene using an injection molding process. However, other materials and processes may be used without departing from the scope of the present invention.

Integrated system 100 may further include a sampling device which the user may use to obtain a sample for testing. The sampling device may be adapted to obtain a biological sample. For instance, the sampling device may be a lancing device that the user may use to draw blood, e.g., for a diagnostic test of blood glucose level.

An exemplary integrated system incorporating a lancing device 360 is shown in FIG. 3. Exemplary lancing device 360 includes a rearward body 312, a finger cover 314, an exterior nozzle 318, an interior nozzle 322 and a trigger 324. Exemplary lancing device 360 further includes an internal spring (not shown) that is used to propel lancet 320 beyond contact surface 321 and through the skin to depth selected by the user.

As shown in FIG. 3, the exemplary lancing device 360 is connected to container 110. Lancing device 360 may be permanently connected to the container, for instance, by forming, e.g., rearward body 312, finger cover 314, exterior nozzle 318 or interior nozzle 322 integrally with the container 110, or by bonding one of these components to the container 110, e.g., by a mechanical attachment (clips, brackets, tabs, slots), bonding, gluing, and welding. As would be apparent to one of ordinary skill in the art, other known expedients can be used. Alternatively, lancing device 360 may be releasably connected to the container 110 by providing corresponding releasable connectors on lancing device 360 and container 110. For example, lancing device 360 may be provided with one or more slots, holes, cavities, enclosures, or clips that engage corresponding structures on container 110, or vice versa. As illustrated in FIG. 18, a holder clip 608 can be stretched over container 110 for a snug fit. Holder clip 608 includes a clip that can releasably engage lancing device 360 in place. Similarly, FIG. 19 embodies holder holes 610 designed to engage the container 110 and the lancing device 360 together on one attachment. One having ordinary skill in the art will understand that other types of holders can be used to receive one or more devices used for diagnostic testing, such as brackets, magnets, bayonet locks, slots, tabs, hook and loop fasteners, etc. As further alternatives, lancing device 360 may be connected to housing 131 of meter 130, or to closure portion 140. Preferably only one of the rearward body 312, finger cover 314, exterior nozzle 318 or interior nozzle 322 is connected to the container 110 so that lancing device 360 may be adjusted and used without disconnecting it from the container 110.

In order to draw a sample using exemplary lancing device 360, the user may first select a desired depth of penetration of lancet 320 by rotating exterior nozzle 318 so that the desired depth indicator 326 on exterior nozzle 318 is aligned with arrow 328 on interior nozzle 322. Next, the user loads the internal spring by pulling interior nozzle 322 away from rearward body 312 and places contact surface 321 against the surface to be lanced. The user may then actuate trigger 324 to release the internal spring, which propels lancet 320 beyond contact surface 321 to the indicated depth, and thus into the skin. A blood sample can then be applied to the sample chamber 121 of test strip 120.

Further details of exemplary lancing device 360 are shown in prior application Ser. No. 10/757,776, entitled "LANCING DEVICE," filed Jan. 15, 2004, having assignee in common with the instant application, which is incorporated by reference herein in its entirety. However, the present invention is not limited to any particular sampling device, and one of skill in the art will recognize that other sampling devices can be incorporated in a manner similar to the exemplary lancing device described above.

2. Meter Electronics

Figure 4:
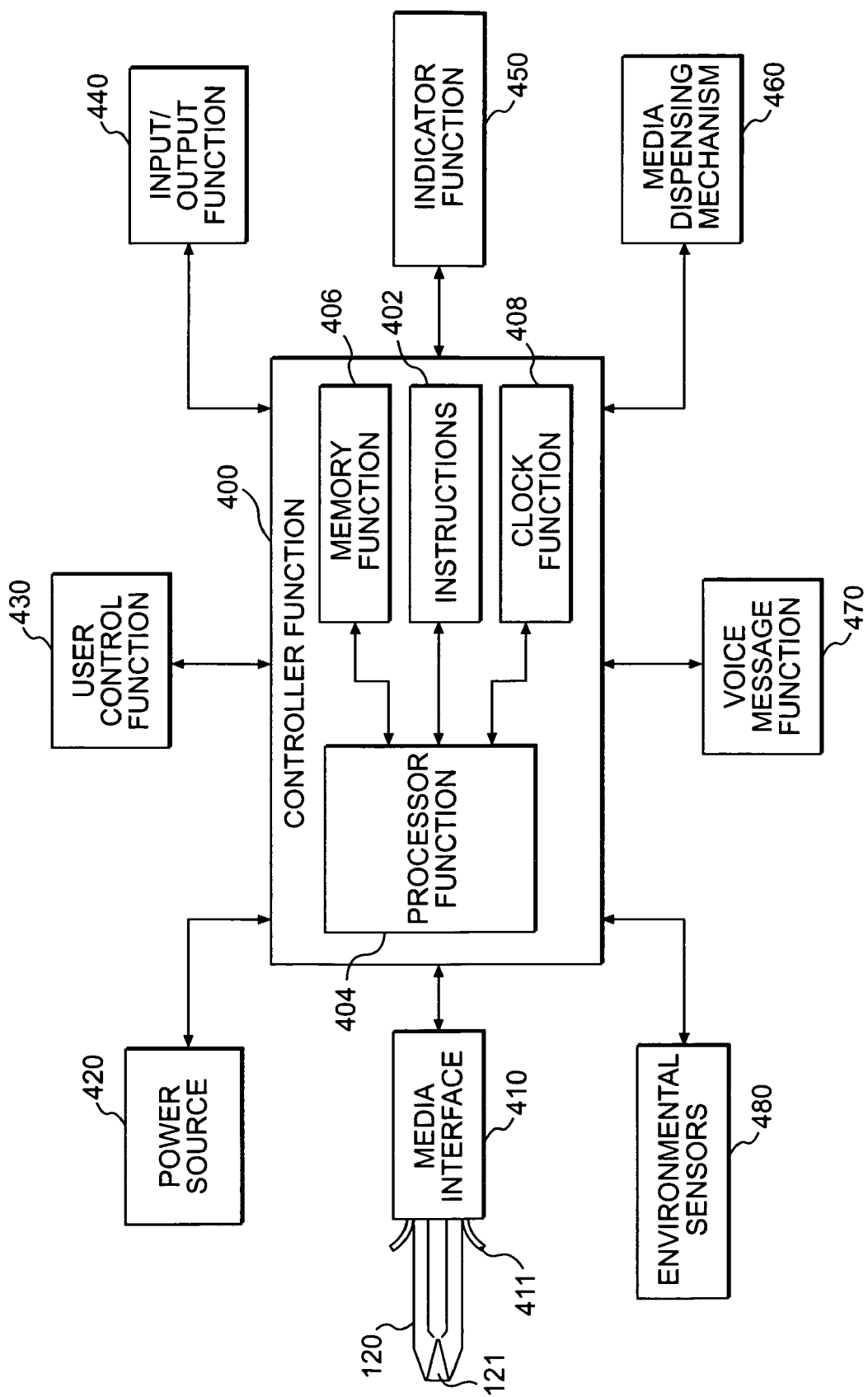
FIG. 4 is a block diagram illustrating the functional components of a diagnostic meter consistent with the present invention.

FIG. 4 shows is a block diagram illustrating functional components of exemplary meter 130. As shown in FIG. 4, meter 130 may include controller function 400, media interface 410, power source 420, user control function 430, input/output function 440, indicator function 450, media dispensing mechanism 460, voice message function 470, and environmental sensors 480. Although not illustrated in FIG. 4, in at least one embodiment, the media interface 410 may include all the structure necessary for implementation of an on-strip coding arrangement as later described with regard to FIGS. 15-22. For example, the media interface 410 may include the first plurality of connector contacts 738 and the second plurality of connector contacts 740 as described more fully below. Accordingly, the following example combines the benefits of an on-strip coding system, as will be described in more detail below, and the benefits of an integrated meter 130 and container 110 arrangement. In an illustrative embodiment, the functional components of meter 130 are contained within meter housing 131. However, it will be understood that some or all of the components of a given function may be located elsewhere in integrated system 100.

Controller 400 controls the operation of the functional components of the meter in accordance with its instructions 402, which may be provided as software or firmware. Controller 400 may include processor 404, memory 406, and clock 408 functions. In an illustrative embodiment of the invention, the processor 404, memory 406, and/or clock 408 functions may be implemented using an Application Specific Integrated Circuit (ASIC), which allows controller 400 to be reduced in size in comparison to standard integrated circuit technology. However, it will be understood that the controller may be implemented using standard integrated circuit technology, or other technology, without departing from the scope of the present invention.

Processor function 404 executes instructions 402 used to control the functional components 410-480 of meter 130. In particular, processor 404 executes instructions 402 necessary to perform the diagnostic test (e.g., as set forth in U.S. Pat. Nos. 6,743,635 and 6,946,299, incorporated by reference above). The instructions 402 for the processor 404 may be stored in memory 406 or elsewhere. Memory function 406 may also store data, such as calibration data and other data used in the performance of the diagnostic test. In exemplary embodiments of the present invention, memory 406 is used to store results of the diagnostic test, together with a time/date data and/or associated voice message, for later review or uploading (discussed below).

Clock function 408 regulates the processor's execution of the instructions 402 in time. In particular, clock function 408 is used to regulate the timing of steps in the diagnostic test. For instance, processor 404 may use clock 408 to regulate an incubation time period, or other time periods, necessary for the correct performance of the diagnostic test (e.g., as set forth in U.S. Pat. Nos. 6,743,635 and 6,946,299, incorporated by reference above). Clock function 408 may be implemented by a single system clock or by multiple clocks for different purposes.

Media interface 410 accepts test media, such as test strips 120, for testing and includes a channel 411 to ensure that the test media is correctly positioned when inserted by a user or media dispensing mechanism 460. Interface 410 includes one or more media sensors for determining, e.g., whether a test strip 120 has been correctly inserted in the test port 410 (i.e., whether interface side 122 of test strip 120 is properly positioned with respect to the media sensors); whether an adequately-sized sample has been applied to the sample chamber on the sample side 121 of the test strip; and the presence or concentration of analyte in the sample. For meters using electrochemical techniques, the media sensors may include one or more electrical contacts corresponding to electrodes on the interface side 122 of test strip 120. For meters using photometric techniques, at least the presence or concentration of analyte in the sample is determined using an optical sensor, e.g., a LED and corresponding photo-detector.

Power source 420 provides power to the electronic components of meter 130. In an illustrative embodiment, the power source is a lithium coin cell battery. However, other power sources, such as other types of batteries, solar cells, or AC/DC converters may be used without departing from the scope of the present invention. The output of the power source may be regulated, e.g., by a voltage regulator circuit.

User control function 430 may include, for example, one or more buttons, switches, keys or other controls for controlling the functions of meter 130. In an illustrative embodiment, user control function 430 is implemented by one or more buttons 132 placed on the left side of meter housing 131 (see FIG. 1). In this position, button 132 may be comfortably pressed with the right thumb or index finger while the integrated system 100 is held in the right hand, with display 133 in an upright position. However, user control 430 may be positioned elsewhere on meter 130. For example, button 132 may be placed on right hand side of the meter housing 131 in order to be more convenient for left handed users, or on the top of the meter, e.g., centered under display 133. As another example, user control function 430 may include a switch actuated when the user opens the closure 140, e.g., so that the meter 130 automatically turns on when the user opens container 110 to retrieve a test strip.

In an exemplary embodiment of the present invention, user control function 430 is implemented using a single control, e.g., a single button 132, that is used to control a plurality of meter functions. For example, user control 430 may be used to control the input/output 440 function, indicator function 450, media dispensing mechanism 460, and/or voice message function 470 by providing commands to these functions directly or through controller 400. User control 430 may also be used to control the diagnostic test function of controller 400. For example, when a test is to be performed using a control solution (e.g., as set forth in U.S. Pat. Nos. 6,743,635 and 6,946,299, incorporated by reference above), button 132 may be held down to indicate to controller 400 that the current sample is of a control solution and, consequently, that controller 400 should perform a control test on the current strip.

Alternatively, a plurality of user controls, e.g., a plurality of buttons 132, may be provided, with each button having different functions. For example, two buttons may be provided to allow a user to scroll through diagnostic test results stored in memory 406 in either forward or reverse directions. As an aid to the user, the function of the button or buttons 132 at the particular time may be dynamically indicated by indicator function 450. For example, when reviewing previous test results, indicator function 450, e.g., a display 133, may instruct the user to "PRESS BUTTON TO VIEW NEXT RESULT." Further, user controls 430 may have different functions at different times. For example, holding button 132 down upon the insertion of a test strip into media interface 410 may command the controller to perform a control test on that strip, while holding the button down without inserting a test strip may command the controller to display the result of the previous diagnostic test.

Input/output function 440 provides for the downloading of data or instructions 402 to meter 130, and/or the uploading of data from meter 130. Input/output function 440 may be used, for example, to upload the results of a diagnostic test or tests so that they may be transferred to a storage device or to a third party, e.g., a medical care provider for use in treating the user. Alternatively, input/output function 440 may be used to download data (e.g., calibration data) or instructions 402 (e.g., updated software) to the meter 130. Input/output function 440 may be implemented using any conventional digital or analog information interface, e.g., a serial port, a parallel port, an optical port, an infrared interface, etc.

Indicator function 450 indicates the result of the diagnostic test to the user, e.g., as a numerical value together with the units of measurement. In addition to indicating the result of the diagnostic test, the indicator may present other information to the user. For example, the indicator 450 may indicate the average result of a plurality of tests, the time and/or date, remaining battery life, etc. (e.g., as set forth in U.S. Pat. Nos. 6,743,635 and 6,946,299, incorporated by reference above). Indicator 450 may also be used to prompt the user to perform certain steps of the diagnostic test, e.g., to apply the sample to the test strip 120. In an exemplary embodiment of the present invention (discussed below), indicator 450 indicates the number of test strips remaining in container 110, or the number of tests or the time remaining before meter 130 becomes inoperative.

Figure 12:
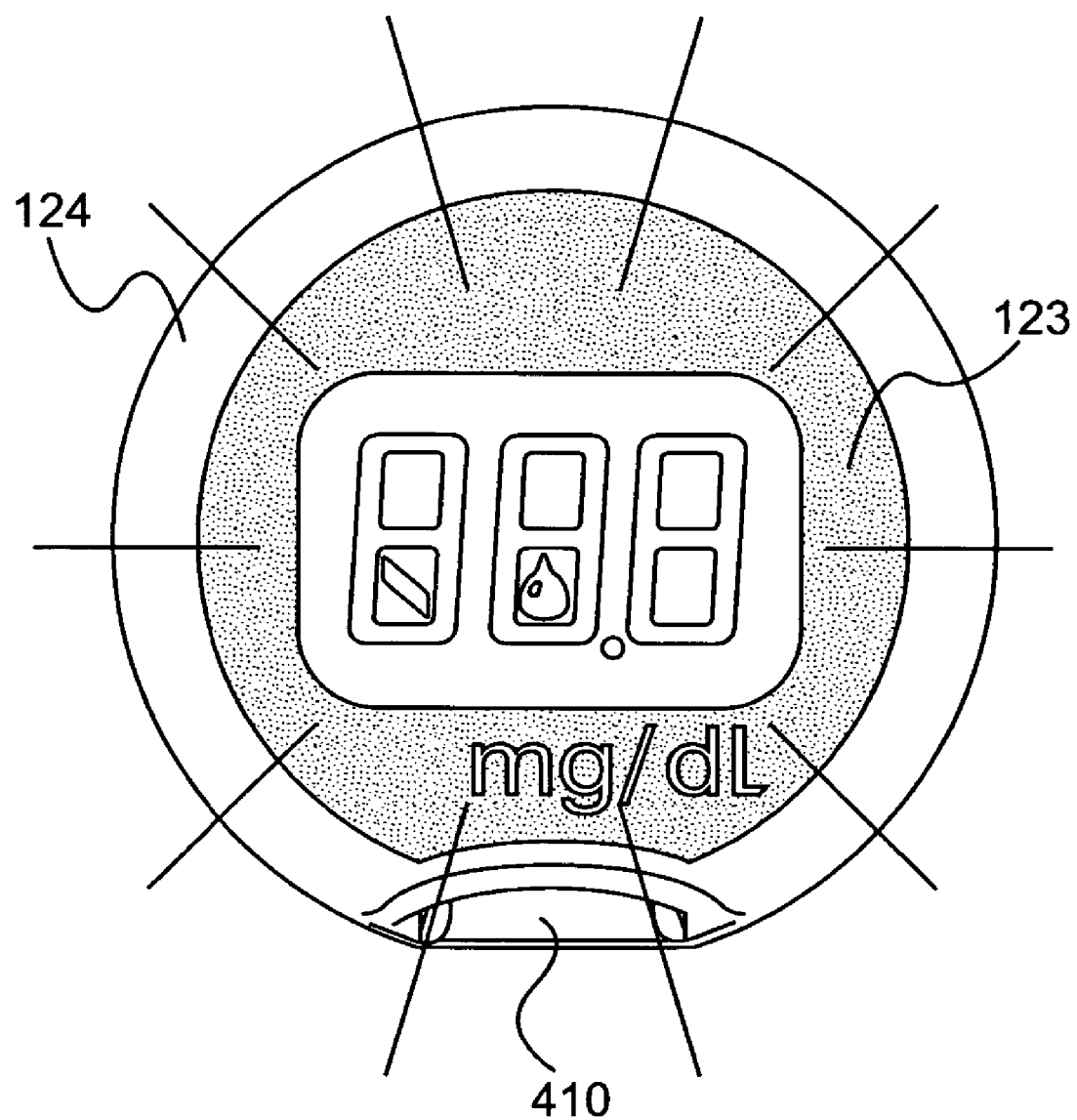
FIG. 12 is a perspective view of a top portion of a container housing comprising a backlit display and a ring-portion.
Figure 13:
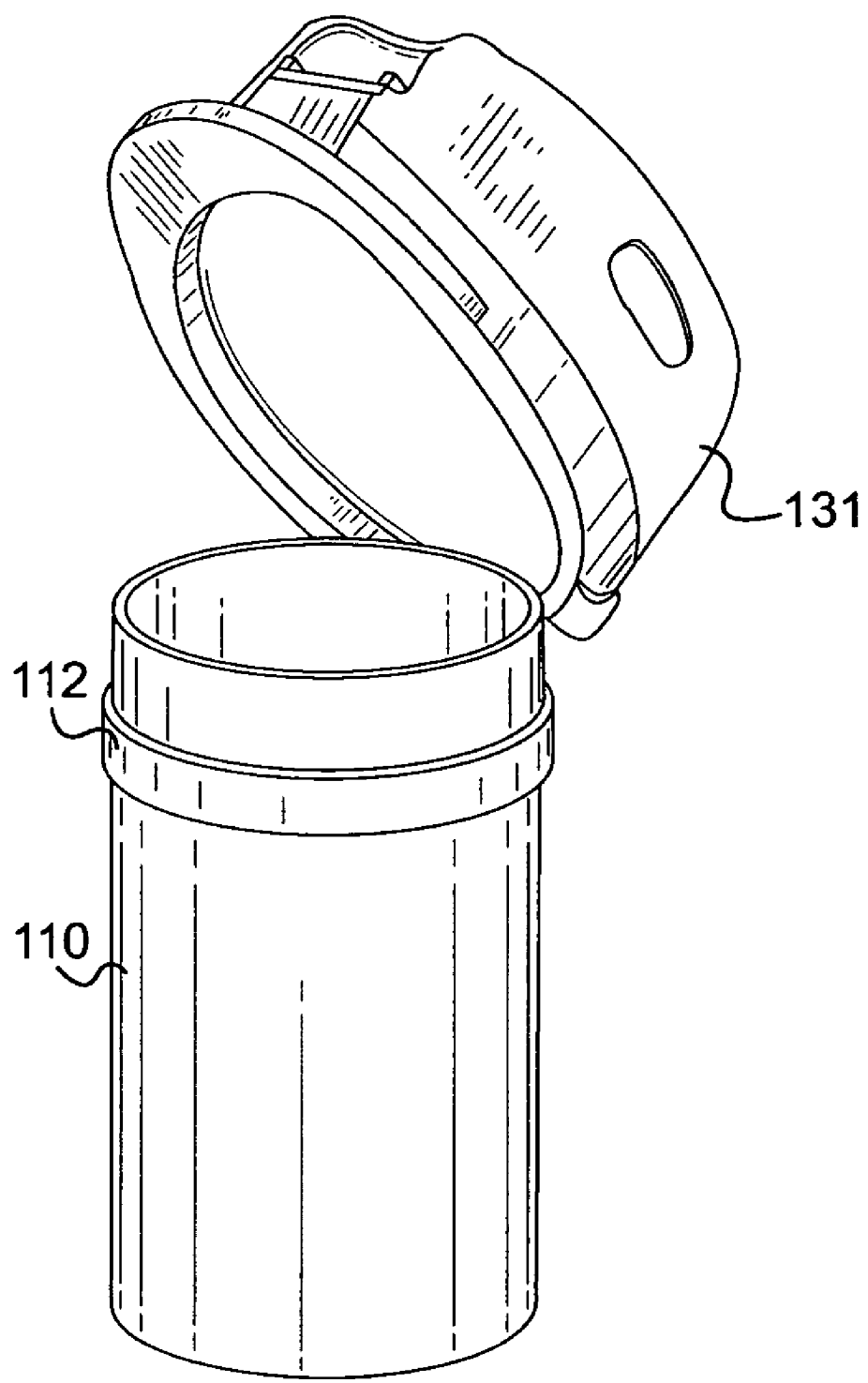
FIG. 13 is a perspective view of an open container with an illuminated flange.

Indicator function 450 may present information in visible, audible or tactile form. For example, indicator 450 may include a display 133 for displaying information, e.g., using numerical values, words and/or icons. A number of different technologies may be used for display 133. For example, the display may be a liquid crystal display, a vacuum fluorescent display, an electroluminescent display, a LED display, a plasma display, etc. In an illustrative embodiment, display 134 is a liquid crystal display. In addition, as illustrated in FIG. 12, indicator function 450 may include a backlit display 123 to light the insertion point of the test strip 120 when it is inserted into test port 410. Furthermore, a top ring-portion 124 of housing 131 can be optically coupled to the backlit display 123 and constructed with a colored transparent molded piece that light-pipes from either the backlight or a vial-light LED 253 (FIGS. 7-9) to improve visibility if the test strip 120 is inserted in a poorly lit area. In addition, as illustrated in FIG. 13, flange 112 is also constructed with a transparent molded piece that lights up as the container 110 is opened.

Alternatively or in addition, indicator 450 may include an audible indicator configured to indicate information by sound. For example, indicator 450 may include a speaker connected to a voice and/or sound circuit that is configured to, e.g., speak the result of the diagnostic test or to beep to indicate that an error has occurred. In addition, indicator 450 may be linked with a particular FM radio frequency in order to provide an audible output on a user's FM radio. Similarly, the indicator 450 could be linked with any personal electronic device, such as, for example, an MP3 player, a cell phone, handheld computing system, or BLACKBERRY device etc. in order to present testing information to a user. As a further alternative, indicator 450 may be implemented as a dynamic Braille indicator for use by the blind.

In an illustrative embodiment, indicator function 450 includes a display 133 as well as a speaker connected to a sound circuit (not shown). The display 133 may be placed on the top of meter housing 131 as shown in FIGS. 1 and 3. In this position, display 133 is conveniently visible when the meter is grasped in the hand with the thumb or index finger on button 132.

Because the diagnostic test media, e.g., test strips 120, is typically very small, certain users may find it difficult to retrieve the test media from the container 110. Accordingly, a media dispensing mechanism may be used to provide for the automated dispensing of test media from the container.

Figure 5:
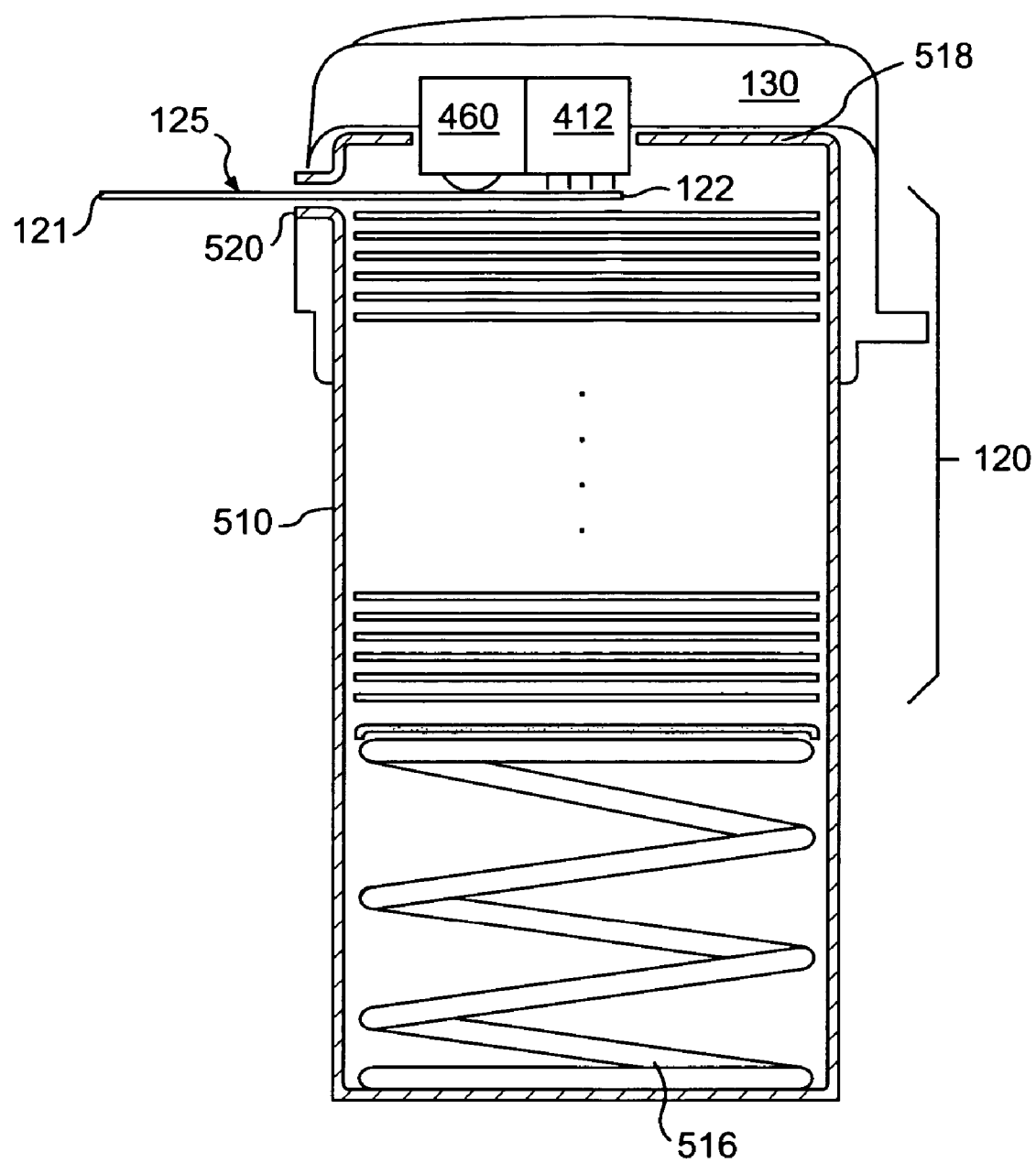
FIG. 5 is a cross-sectional view of an integrated fourth embodiment of an integrated system consistent with the present invention.

FIG. 5 shows a cross-section of an exemplary integrated system having a media dispensing mechanism 460. In this embodiment, the container is configured as a spring-loaded magazine 510. A plurality of test strips 120 are stacked on top of one another in magazine 510. Magazine 510 may have an interior shape similar to that of the test media in order to maintain the alignment of the stack. For example, for the test strips 120 depicted in FIG. 1, the interior of magazine 510 may be generally rectangular in cross-section.

Spring 516 pushes the stack of test strips against the top 518 of magazine 510, where the top test strip 125 is operably positioned with respect to strip dispensing mechanism 460. Dispensing mechanism 460 dispenses the top test strip 125 in the stack using a linear and/or rotational mechanical action. The mechanical action may be executed manually (e.g., by the user pulling a slide or rotating a wheel) or by a motor (e.g., a stepper motor) actuated by user control function 430. The top test strip 125 is slid from the stack and through slot 520. The test media used with this embodiment may be modified by application of a non-friction coating or film, such as TEFLON, to one or both sides in order to ensure smooth ejection.

Where the particular diagnostic test requires that the test strip be inserted into the media interface 410 before the sample is applied, media dispensing mechanism 460 may position the interface side 122 of the ejected test strip 125 within media interface 410, e.g., with the interface side 122 of the test strip engaging the media sensors and the sample chamber 121 of the test strip projected outwardly from the meter 130 so as to allow application of a sample, as shown in FIG. 5. Alternatively, media dispensing mechanism 460 may simply present either end of the top test strip 125 to the user, who may then manually insert the test strip 125 into media interface 410 (either before or after the sample is applied, depending on the requirements of the particular diagnostic test). Controller 400 may be instructed to count the number of test strips 120 dispensed by media dispensing mechanism 460 and cause indicator function 450 to indicate, e.g., the number of test strips 120 remaining in magazine 510.

Voice message function 470 may be used to record a voice message associated with a given diagnostic test result. For self-testing of blood glucose level, for example, a user may use voice message function 470 to record information related to their diet around the time of the diagnostic test. The voice message may be recorded in memory 406 along with a pointer associating it with a particular test result. The use of the voice message function 470 is more fully explained in prior application Ser. No. 10/764,974, entitled "MEDICAL DIAGNOSTIC TESTING DEVICE WITH VOICE MESSAGE CAPABILITY," filed Jan. 26, 2004, having assignee in common with the present application, which is incorporated by reference herein in its entirety. At the end of the useful life of the meter 130, meter 130 itself may be given or sent to the user's medical care provider. The medical care provider may then review the results of the diagnostic tests and/or associated voice messages for use in treating the user.

Environmental sensing function 480 may include one or more environmental sensors used to gather data used in the performance of the diagnostic test. Such environmental sensors may include, e.g., a temperature sensor and/or a humidity sensor. For example, meter 130 may use a temperature reading to correct the diagnostic test result for temperature dependence (e.g., as set forth in U.S. Pat. Nos. 6,743,635 and 6,946,299, incorporated by reference above). As a further example, meter 130 may use a humidity reading to determine if the humidity level is too high to proceed with the diagnostic test.

3. Prevention of the Use of Incorrect Test Strips

Meter 130 may be calibrated for use with a particular brand or manufacturer's lot of test media by customizing the diagnostic test performed by meter 130 with respect to the particular brand or lot using one or more calibration parameters. These calibration parameters may include environmental corrections (e.g., temperature corrections), timing period corrections (e.g., with respect to incubation time), voltage corrections (e.g., for use in electrochemical tests), color variations (e.g., for use in photometric tests), etc., that customize the diagnostic test function of controller 400 to the particular brand or lot of test media. See, e.g., U.S. Pat. Nos. 6,743,635 and 6,946,299, incorporated by reference above.

In an illustrative embodiment of the present invention, integrated system 100 includes one or more containers 110 or magazines 510 of test strips 120 packaged together with a meter 130. The test strips 120 in the package are from the same manufacturing lot or otherwise have the same characteristic reaction to blood glucose so that meter 130 may be calibrated once and thereafter used with any of the test strips 120 in the package without recalibration.

The diagnostic test function of the packaged meter 130 may be precalibrated by the manufacturer or distributor, e.g., by providing instructions 402 and/or data customized to the associated test media. Alternatively, meter 130 may be calibrated at the user level by requiring the user to calibrate the meter with respect to a particular brand or lot of test media prior to using the meter to conduct diagnostic tests. For example, the user may use the user control 430 or input/output 440 functions to enter or download calibration data or a code from which controller 400 may derive calibration data. In another approach, each test media container 110 (or a co-packaged group of containers from the same lot) may be provided with a data storage device that stores the calibration data electronically. See, e.g., U.S. Pat. Nos. 6,743,635 and 6,946,299, incorporated by reference above.

In the event the test strips 120 in the package are not from the same manufacturing lot or otherwise do not have the same characteristic reaction to blood glucose, users may forget to calibrate the meter 130 for use with a new brand or lot of test media. Accordingly, the present invention allows the meter 130 to be removed from the test strip container 110 and transferred to another container by using several different coding techniques that prevent erroneous results that could have serious consequences for the user if the meter 130 is incorrectly calibrated. As long as the meter is properly associated with a coding container for strips of a matched lot, the user does not need to take further action to program the meter.

3a. On-Strip Coding Example

In one illustrative embodiment, common coding errors associated with forgetting to change a code chip or button code are prevented by the method of on-strip coding. This method is carried out on the test strip 120 provided to the meter 130. A set lot code parameter that corresponds to the specific test strip lot is selected from the meter's memory 406. On-strip coding is similar to universal coding in that this method is also not technique dependent and saves the cost of disposing the meter 130 with each vial of strips 120.

With regard to on-strip coding, the individual test medium, such as, for example, a single test strip 120 may include an embedded code, readable by the meter 130, relating to data associated with a lot of test strips, or data particular to that individual strip 120. The embedded information presents data readable by the meter signaling the meter's microprocessor to access and utilize a specific set of stored calibration parameters particular to test media/medium from a manufacturing lot to which the individual strip belongs, or to an individual test strip. In this approach, the same calibration parameters noted above (e.g., parameters related to environmental corrections, timing period corrections, voltage corrections, and/or color variations, etc.) can be individually provided on a particular test medium (as opposed to a code associated with container 110) and directly read by controller 400 without the hazards of human error.

In one approach, each test strip 120 is embedded with an individual code that corresponds to a pattern of electrical contacts formed at the interface side 122 of test strip 120. Upon operative connection of the individual test strip 120 with the meter 130, the meter is presented with, and reads from the contacting pads at the interface side 122, a particular code representing information signaling the meter 130 to access data related to the underlying test strip 120. The coded information may signal the meter to access data including, but not limited to, parameters indicating the particular test to be performed, parameters indicating connection to a test probe, parameters indicating connection to a check strip, calibration coefficients, temperature correction coefficients, ph level correction coefficients, humidity correction, hematocrit correction data, and data for recognizing a particular test strip brand.

The incorporation of individualized code data within individual test strips provides numerous advantages in addition to those associated with accuracy of measurement. For example, with individual strip coding a user no longer needs to manually enter the meter's lot code, thereby removing the possibility of user error for this critical step. Strip lot codes stored directly on individual test strips will also provide a means to ship mixed lots of strips in a single strip vial. In contrast, current technologies such as button/key coding require all strips (typically packaged in a vial including 50 strips from the same lot) in a vial to be from the same lot code.

Individual strip coatings representing particular codes also afford bulk packaging benefits. For example, mixed lot test strips and vials including different numbers of strips will be possible. Strips from various lots could be stored in a central location and packaged for sale without the time and expense of strips are packaged from a single lot. Individual lot calibration codes stored on strips can also provide a means for varying a code across a single lot should a strip lot have variation from beginning to end or anywhere in between. Predetermined variations in manufacturing within a strip lot can be corrected by applying a continuously changing code across the lot, thereby solving yield problems and improving in-lot strip to strip variation. In addition, embedding lot codes on individual strips can be used to distinguish different types of test strips (e.g. glucose vs. ketone), check strips, or different manufacturing procedures, provide data for meter upgrades, to correlate particular test strips for use only with a specific meter or meter type, or, as will be described in more detail below, to provide data related to a particular preventive measure.

The following disclosure provides one example of a particular on-strip coding arrangement for use in a system employing an electrochemical technique. In addition, the following example combines the benefits of an on-strip coding system with the benefits of an integrated meter 130 and container 110 arrangement, as previously described. As noted above, although the present invention has been illustrated as utilizing test media in the form of test strips 120, exemplary embodiments of the present invention are not limited to a particular type of media. Those of skill in the art will recognize that the principles of the present invention, including on-strip coding examples, are equally applicable to diagnostic testing systems using alternative techniques and those employing test media in other forms, e.g., tabs, discs, etc.

Test media can be manufactured to include a sample chamber for receiving a user's fluid sample, such as, for example, a blood sample. The sample chamber and test strip of the present specification can be formed using materials and methods described in commonly owned U.S. Pat. No. 6,743,635, incorporated by reference above. Accordingly, the sample chamber may include a first opening in the proximal end of the test strip and a second opening for venting the sample chamber. The sample chamber may be dimensioned so as to be able to draw the blood sample in through the first opening, and to hold the blood sample in the sample chamber, by capillary action. The test strip can include a tapered section that is narrowest at the proximal end, or can include other indicia in order to make it easier for the user to locate the first opening and apply the blood sample.

A working electrode and counter electrode can be disposed in the sample chamber optionally along with fill-detect electrodes. A reagent layer is disposed in the sample chamber and preferably contacts at least the working electrode. The reagent layer may include an enzyme, such as glucose oxidase, and a mediator, such as potassium ferricyanide or ruthenium hexamine. The test strip has, near its distal end, a first plurality of electrical strip contacts that are electrically connected to the electrodes via conductive traces. In addition, the test strip may also include a second plurality of electrical strip contacts near the distal end of the strip. The second plurality of electrical contacts can be arranged such that they provide, when the strip is inserted into the meter, a distinctly discernable lot code readable by the meter. As noted above, the readable code can be read as a signal to access data, such as calibration coefficients, from an on-board memory unit in the meter related to test strips from that lot, or even information corresponding to individual test strips.

The meter may be battery powered and may stay in a low-power sleep mode when not in use in order to save power. When the test strip is inserted into the meter, the first and second plurality of electrical contacts on the test strip contact corresponding electrical contacts in the meter. The second plurality of electrical contacts may bridge a pair of electrical contacts in the meter, causing a current to flow through the a portion of the second plurality of electrical contacts. The current flow through the second plurality of electrical contacts causes the meter to wake up and enter an active mode. The meter also reads the code information provided by the second plurality and can then identify, for example, the particular test to be performed, or a confirmation of proper operating status. In addition, the meter can also identify the inserted strip as either a test strip or a check strip based on the particular code information. If the meter detects a check strip, it performs a check strip sequence. If the meter detects a test strip, it performs a test strip sequence.

In the test strip sequence, the meter validates the working electrode, counter electrode, and, if included, the fill-detect electrodes, by confirming that there are no low-impedance paths between any of these electrodes. If the electrodes are valid, the meter indicates to the user that sample may be applied to the test strip. The meter then applies a drop-detect voltage between the working and counter electrodes and detects a fluid sample, for example, a blood sample, by detecting a current flow between the working and counter electrodes (i.e., a current flow through the blood sample as it bridges the working and counter electrodes). To detect that an adequate sample is present in the sample chamber and that the blood sample has traversed the reagent layer and mixed with the chemical constituents in the reagent layer, the meter may apply a fill-detect voltage between the fill-detect electrodes and measures any resulting current flowing between the fill-detect electrodes. If this resulting current reaches a sufficient level within a predetermined period of time, the meter indicates to the user that adequate sample is present and has mixed with the reagent layer.

The meter can be programmed to wait for a predetermined period of time after initially detecting the blood sample, to allow the blood sample to react with the reagent layer or can immediately begin taking readings in sequence. During a fluid measurement period, the meter applies an assay voltage between the working and counter electrodes and takes one or more measurements of the resulting current flowing between the working and counter electrodes. The assay voltage is near the redox potential of the chemistry in the reagent layer, and the resulting current is related to the concentration of the particular constituent measured, such as, for example, the glucose level in a blood sample.

In one example, the reagent layer may react with glucose in the blood sample in order to determine the particular glucose concentration. In one example, glucose oxidase is used in the reagent layer. The recitation of glucose oxidase is intended as an example only and other materials can be used without departing from the scope of the invention. Other possible mediators include, but are not limited to, ruthenium and osmium. During a sample test, the glucose oxidase initiates a reaction that oxidizes the glucose to gluconic acid and reduces the ferricyanide to ferrocyanide. When an appropriate voltage is applied to a working electrode, relative to a counter electrode, the ferrocyanide is oxidized to ferricyanide, thereby generating a current that is related to the glucose concentration in the blood sample. The meter then calculates the glucose level based on the measured current and on calibration data that the meter has been signaled to access by the code data read from the second plurality of electrical contacts associated with the test strip. The meter then displays the calculated glucose level to the user. Each of the above-described components and their interconnection will now be described.

Figure 15:
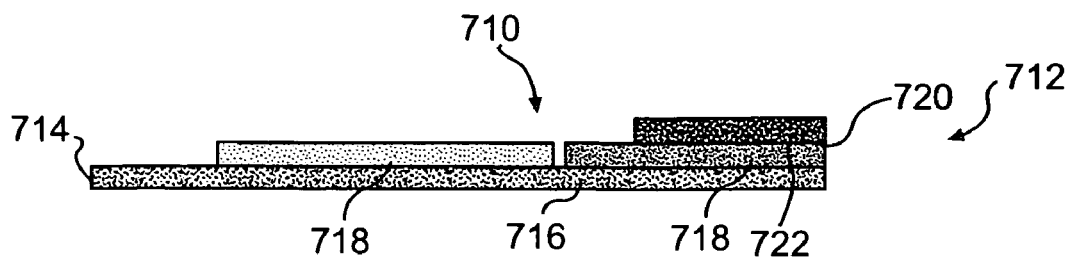
FIG. 15 is a general cross-sectional view of a test strip according to an embodiment of the present invention.

FIG. 15 illustrates a general cross-sectional view of an embodiment of a test strip 710. Test strip 710 includes a proximal connecting end 712, a distal end 714, and is formed with a base layer 716 extending along the entire length of test strip 710. Base layer 716 is preferably composed of an electrically insulating material and has a thickness sufficient to provide structural support to test strip 710. For purposes of this application, an insulating material (e.g. an insulating layer, coating, ink, or substrate etc.) comprises any material in which electrons or ions cannot be moved easily, hence preventing the flow of electric current. Accordingly, an element can be said to be insulated when it is separated from other conducting surfaces by a dielectric substance or air space permanently offering a high resistance to the passage of current and to disruptive discharge through the substance or space. By contrast, for purposes of this application, a resistive element, is one that introduces an increased level of impedance into a circuit that reduces (but does not necessarily prevent) the flow of electric current. Base layer 16, for example, may be polyester that is about 0.014 inches think, although other sizes my be used depending on the particular application and manufacturing method. Disposed on base layer 716 is a conductive pattern (not shown).

The conductive pattern includes a plurality of electrodes disposed on base layer 716 near proximal end 712, a plurality of electrical strip contacts disposed on base layer 716 near distal end 714, and a plurality of conductive traces electrically connecting the electrodes to the plurality of electrical strip contacts. For purposes of this application, the noun "contact" denotes an area intended for mechanical engagement with another corresponding "contact" irrespective of whether an electric circuit is completed, or passes through the particular area.

In one embodiment, the plurality of electrodes may include a working electrode, a counter electrode, and fill-detect electrodes. The conductive pattern may be applied by applying a conductive material onto base layer 716. The conductive pattern can be applied to the top side of the strip, the bottom side of the strip, or a combination of both. The electrode material may be provided by thin film vacuum sputtering of a conductive material (e.g. Gold) and a semiconductive material (e.g. Indium Zinc Oxide) onto the base layer 716. The resulting electrode layer can then by further patterned according to the specific application by forming particular conductive regions/pathways through a laser ablation process. Alternative materials and methods for providing a conductive pattern in addition to screen printing can be employed without departing from the scope of the invention.

A dielectric insulating layer 718 can be formed over the conductive pattern along a portion of the test strip between the measuring electrodes and the plurality of electrical strip contacts in order to prevent scratching, and other damage, to the electrical connection. As seen in FIG. 15, the proximal end 712 of test strip 710 includes a sample receiving location, such as a sample chamber 720 configured to receive a patient's fluid sample, as described above. The sample chamber 720 may be formed in part through a slot formed between a cover 722 and the underlying measuring electrodes formed on the base layer 716. The relative position of the measuring electrodes and the electrical strip contacts form a proximal electrode region 724 at one end of strip 710 and a distal strip contact region 726 at the other end.

Figure 16:
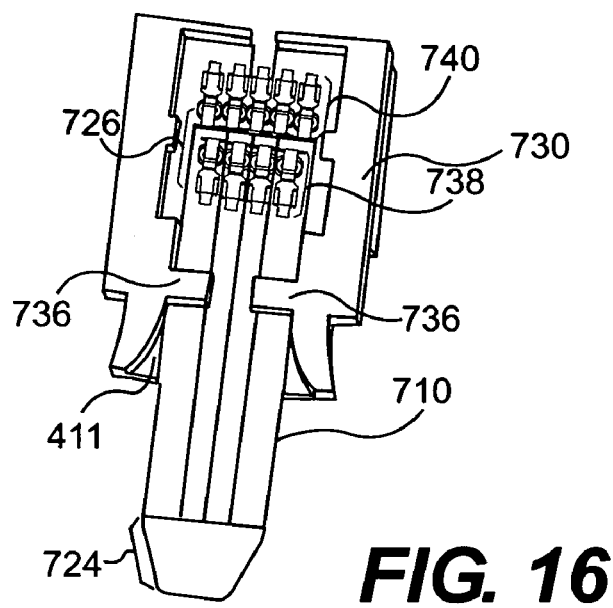
FIG. 16 is a top perspective view of a test strip inserted within a meter strip connector according to an embodiment of the present invention.

Referring to FIG. 16, a top perspective view of a test strip 710 inserted within a meter portion 730 (depicting only a portion of meter 130 from FIG. 1) is illustrated. As seen in FIG. 16, the strip 710 includes a proximal electrode region 724, which contains the sample chamber and measuring electrodes described above. The proximal electrode region 724 may be formed to have a particular shape in order to distinguish to the user, the end receiving a fluid sample from distal strip contact region 726. The meter connector 730 includes channel 411, also depicted in FIG. 4, extending out to a flared opening for receiving the test strip 710. The connector 730 may further include tangs 736 extending a predetermined height above the base of channel 732. The predetermined height of tangs 736 is selected to limit the extent, such as through a corresponding raised layer of test strip 710, to which a test strip 710 can be inserted into channel 732.

Figure 17:
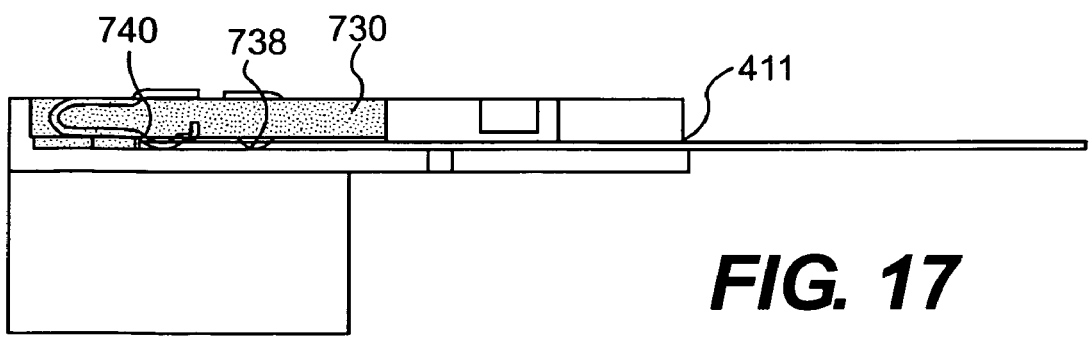
FIG. 17 is a general cross-sectional view of a test strip inserted within a meter strip connector according to an embodiment of the present invention.

The connector portion 730 further includes a first plurality of connector contacts 738, disposed closer to the proximal end of the connector portion 730, and a second plurality of connector contacts 740 disposed closer to the distal end of the connector portion 730. As illustrated, the test strip 710 is inserted into the flared opening with the distal strip contact region 726 extending first through the connector channel 411. With reference to FIG. 17, a general cross-sectional view of a test strip inserted within a meter strip connector portion 730 is illustrated. The channel 411 depicts a proximal row of connectors comprising a first plurality of connector contacts 738. In addition, the channel 411 houses a distal row of connectors comprising a second plurality of connector contacts 740. The connector contacts 738 and 740 make contact with distinct portions of the distal strip contact region 726, as will be described more fully below.

Figure 18A:
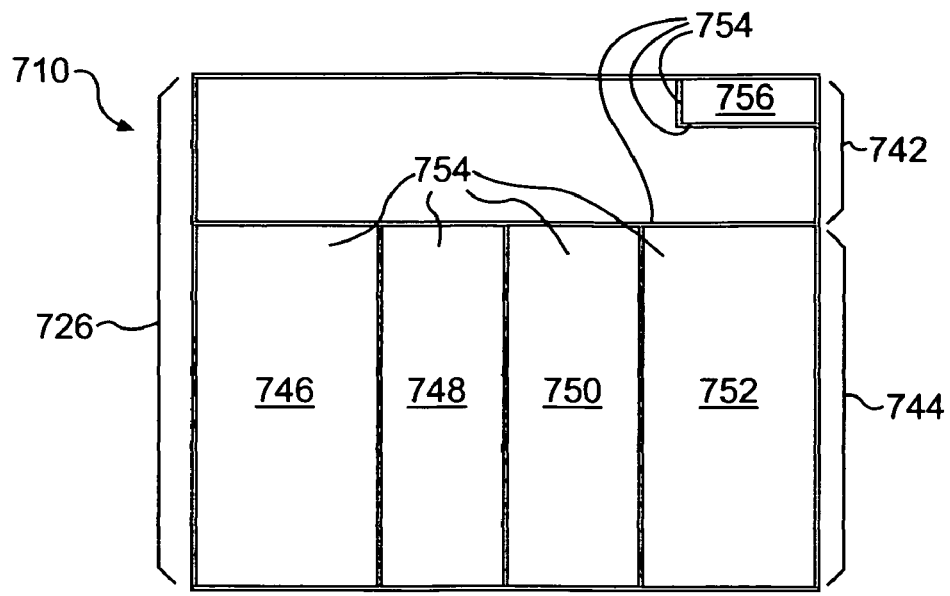
FIG. 18A is a top view of a distal portion of a test strip illustrating breaks dividing particular regions of the test strip connecting end according to an embodiment of the present invention.

FIG. 18A is a top view of a distal portion of a test strip 710 illustrating the distal strip contact region 726. The conductive pattern formed on base layer 716 extends along strip 710 to include the distal strip contact region 726. As illustrated in FIG. 18A, distal strip contact region 726 is divided to form two distinct conductive regions, 742 and 744 respectively. Conductive region 744 is divided into four columns forming a first plurality of electrical strip contacts, labeled 746, 748, 750, and 752 respectively. The first plurality of electrical strip contacts are electrically connected to the plurality of measuring electrodes at the distal end of the test strip 710 as explained above. It should be understood that the four contacts 746-752 are merely exemplary, and the system could include fewer or more electrical strip contacts corresponding to the number of measuring electrodes included in the system.

The first plurality of electrical strip contacts 746-752 are divided, for example, through breaks 754 formed through the underlying conductive pattern in the test strip 710. These breaks could be formed in the conductive pattern during printing, through a scribe process, laser ablated, or through a chemical/photo-etching type process. In addition, other processes of forming conductive breaks by removing a conductor in the test strip 710 may be used as would be apparent to one having ordinary skill in the art. An additional break 754 divides conductive region 744 from conductive region 742 within distal strip contact region 726, and a further break 754 separates the upper right-hand portion of distal strip contact region 726 to form a notch region 756, as will be described more fully in detail below.

Figure 18B:
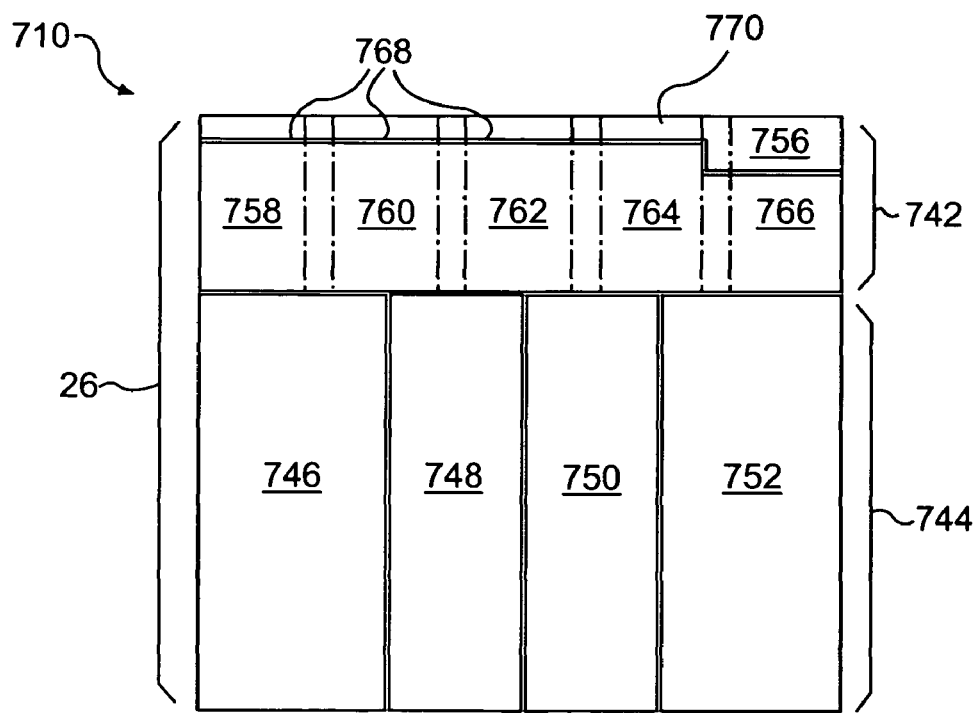
FIG. 18B is a top view of a distal portion of a test strip illustrating conductive regions forming electrical contacts according to an embodiment of the present invention according to an embodiment of the present invention.

FIG. 18B illustrates an additional view of the distal strip contact region 726. In FIG. 18B, conductive region 742, described above with regard to FIG. 18A, is divided into five distinct regions outlining a second plurality of electrical strip contacts forming contacting pads 758, 760, 762, 764, and 766 respectively. The second plurality of electrical strip contacts forming contacting pads 758, 760, 762, 764, and 766, can be divided through the same process used to divide the first plurality of electrical strip contacts, 746, 748, 750, and 752, described above. As noted above, the conductive pattern on base layer 716, which at least in part forms the electrical strip contacts, can be applied to the top side of the strip, the bottom side of the strip, or a combination of both. The contacting pads 758, 760, 762, 764, and 766 are configured to be operatively connected to the second plurality of connector contacts 740 within meter connector 730. Through this operative connection, the meter is presented with, and reads from the contacting pads, a particular code representing information signaling the meter to access data related to the underlying test strip 710. In addition, FIG. 18B depicts a further pattern of breaks 768, isolating an outermost distal connecting end 770 of the distal strip contact region 726.

Figure 18C:
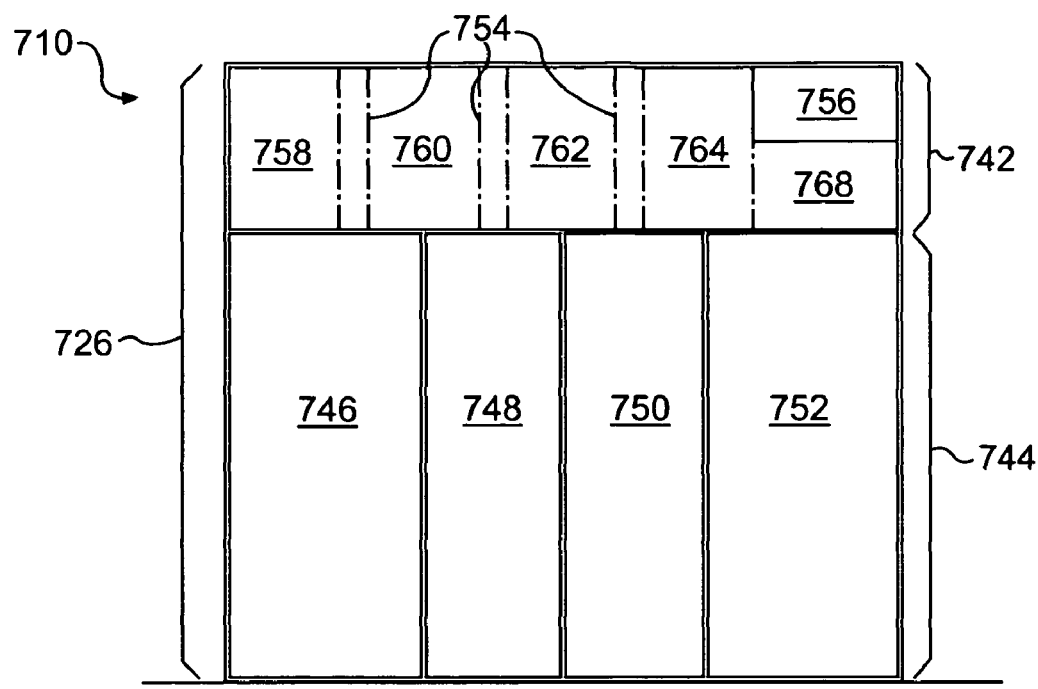
FIG. 18C is a top view of a distal portion of a test strip illustrating a particular arrangement for a plurality of electrical contacts according to an embodiment of the present invention.

FIG. 18C illustrates an additional view of the distal strip contact region 726. In FIG. 18C, the distal strip contact region 726 is depicted to include the first plurality of electrical strip contacts 746-752, the second plurality of electrical strip contacts forming contacting pads 758, 760, 762, 764, and 766, and the separated notch region 756. As noted, the above described conductive regions can all be formed as a result of breaks 754 within the underlying conductive pattern of test strip 710.

Figure 18D:
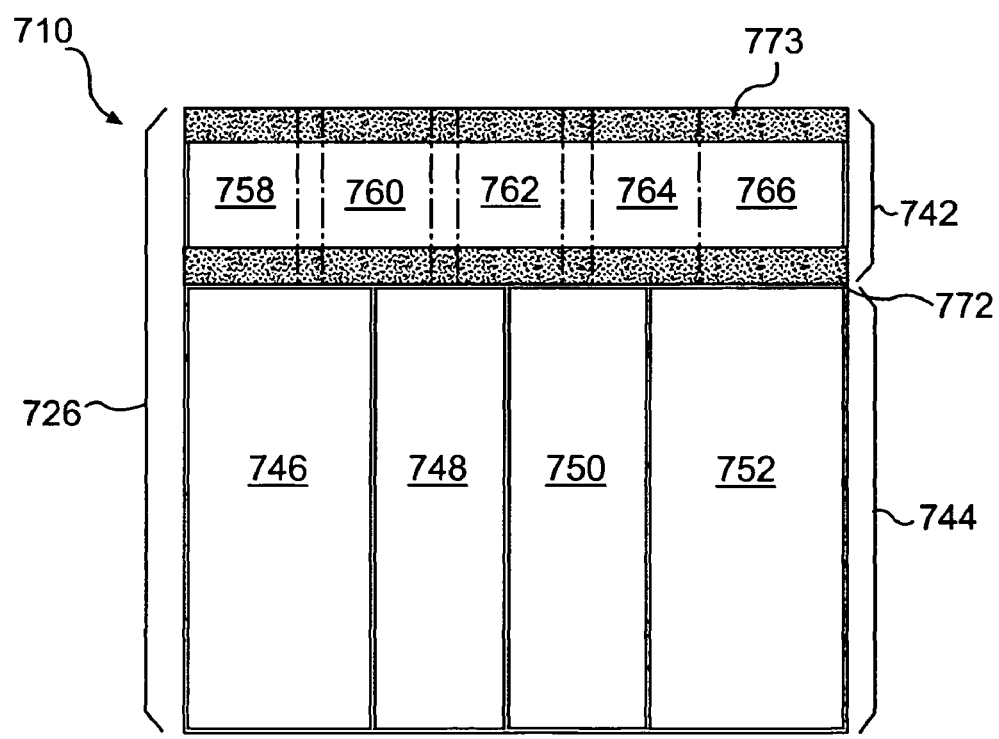
FIG. 18D is a top view of a distal portion of a test strip illustrating multiple insulators covering particular regions of the test strip connecting end according to an embodiment of the present invention.

FIG. 18D illustrates additional features of the distal strip contact region 726. A strip of non-conductive insulating ink 772 can provide further separation between conductive region 744 and conductive region 742 within distal strip contact region 726. The borders between the two regions can be printed with the insulating ink 772 in order to maintain distinct areas of conductivity (bordered by a distinct area of insulation) and to prevent scratching by meter connector contacts during the strip insertion process, which can adversely affect the desired conductivity of one of the strip contacts. The non-conductive insulating ink 772 can be administered, for example, through a screen printing process. Such screen printing of a dielectric insulation coating is advantageous in that it can be applied later on in the strip manufacturing process and in an easily programmable/reproducible pattern. The additional step of adding such an insulating coating can be less expensive and time consuming than methods requiring substrate ablation in some form. For example, ablating a substrate surface through a laser or chemical ablation process involves a time consuming process of precisely removing a particular pattern of preexisting material.

FIG. 18D illustrates that test strip 710 may include another strip of non-conductive insulating ink 773 formed at the distal end of the test strip 710. The strip of non-conductive insulating ink 773 provides a non-conductive region at the distal end of the strip 710. The strip 773 thereby prevents any meter connector contacts from creating an active conductive connection with any portion of contacting pads 758, 760, 762, 764, and 766 before the strip is fully inserted into the meter. Accordingly, strip 773 provides an additional feature for assuring a proper connection between the test strip 710 and the corresponding meter.

Figure 19:
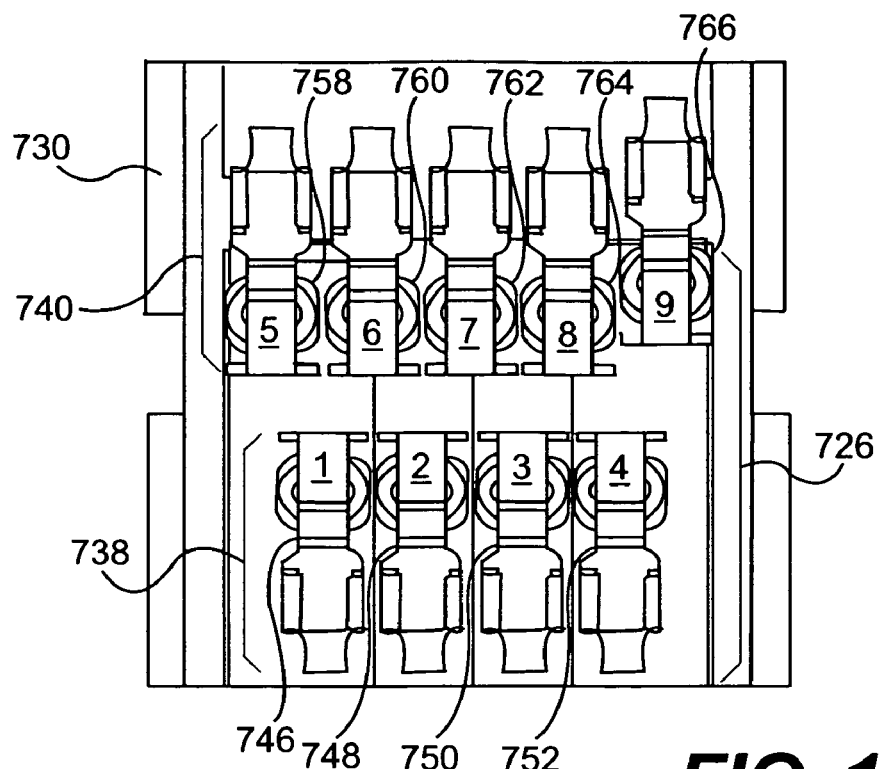
FIG. 19 is an expanded top view of a distal portion of a test strip inserted within a meter strip connector according to an embodiment of the present invention.

Referring to FIG. 19, meter connecter portion 730 is illustrated receiving a distal strip contact region 726 of test strip 710. FIG. 19 depicts a first plurality of connector contacts 738, labeled 1-4 respectively, and a second plurality of connector contacts 740, labeled 5-9. The connector contacts 738 and 740 make contact with distinct portions of the distal strip contact region 726. In particular, upon proper insertion of the test strip 710 into meter connector portion 730, the electrical strip contacts 746-752, which form the first plurality of electrical strip contacts, are respectively electrically connected to the connector contacts 1-4, which form the first plurality of connector contacts 738. Similarly, the contacting pads 758, 760, 762, 764, and 766, which form the second plurality of electrical strip contacts, are respectively electrically connected to the connector contacts 5-9, which form the second plurality of connector contacts 740.

As seen in FIG. 19, the first plurality of connector contacts 738 are laterally staggered or offset, relative to the second plurality of connector contacts 740. Although the first and second plurality are illustrated as being in distinct rows and offset from each other, they need not be in distinct rows and can instead be offset in an additional manner, such as, for example, in distinct groups. Accordingly, as a test strip 710 is inserted into meter connector portion 730, the conductive signal provided by contacting pads 758-766 is unhindered by any scratches or scuffs that would otherwise result from first sliding contacting pads 758-766 under connector contacts 1-4 in order to reach their destination connection at connector contacts 5-9. Therefore, the staggered arrangement of connector contacts 738 relative to connector contacts 740 provides a more reliable connection. In addition, the application of strip 772 of non-conductive insulating ink (FIG. 18D) also assists in preventing the conductive coating from one of contacting pads 758-766 from being scratched and "plowed" away by the friction and interaction from the meter connector contacts 738. Accordingly, strip 772 of non-conductive insulating ink provides increased reliability of connector and contact conduction.

In one embodiment, the connection between contacting pad 766 and connector contact 9 establishes a common connection to ground (or a voltage source where the polarity is reversed), thereby completing an electric circuit, which includes the meter and at least a portion of conductive region 742. The completion of this circuit can perform a meter wake-up function, providing a signal to the meter to power up from low-power sleep mode. Therefore, as illustrated in FIG. 5, the connector contact 9 may be positioned proximally relative to the remaining contacts 5-8, in order to ensure that connectors 5-8 are in proper connecting position prior to the final closing/wake-up of the circuit through the connection of contacting pad 766 and connector contact 9. Furthermore, because the a non-conductive insulating ink strip 773 (See FIG. 18D) can be formed at the distal end of the test strip 710 and also because a conducting substance can be removed from notch region 756 (See FIG. 18C), premature wake-up of the meter will be prevented.

In other words, during distal movement of test strip 710 within the connector channel 411 (See FIGS. 4, 16, and 17), the common connection will not be established at the point connector contact 9 engages the extreme distal edge of test strip 710. Instead, common connection will be established only when the connector contact passes notch 756, and ink strip 773 if applied, and engages a conductive portion of contacting pad 766. Accordingly, the combination of a proximally positioned connector contact 9 and a non-conductive notch region 756 provides a more reliable connection between strip 710 and the meter.

As noted above, the contacting pads 758, 760, 762, 764, and 766 are configured to be operatively connected to the second plurality of connector contacts 740 within meter connector portion 730. Through this operative connection, the meter is presented with, and reads from the contacting pads, a particular code signaling the meter to access information related to a particular underlying test strip 710. The coded information may signal the meter to access data including, but not limited to, parameters indicating the particular test to be performed, parameters indicating connection to a test probe, parameters indicating connection to a check strip, calibration coefficients, temperature correction coefficients, ph level correction coefficients, hematocrit correction data, and data for recognizing a particular test strip brand.

Figure 20:
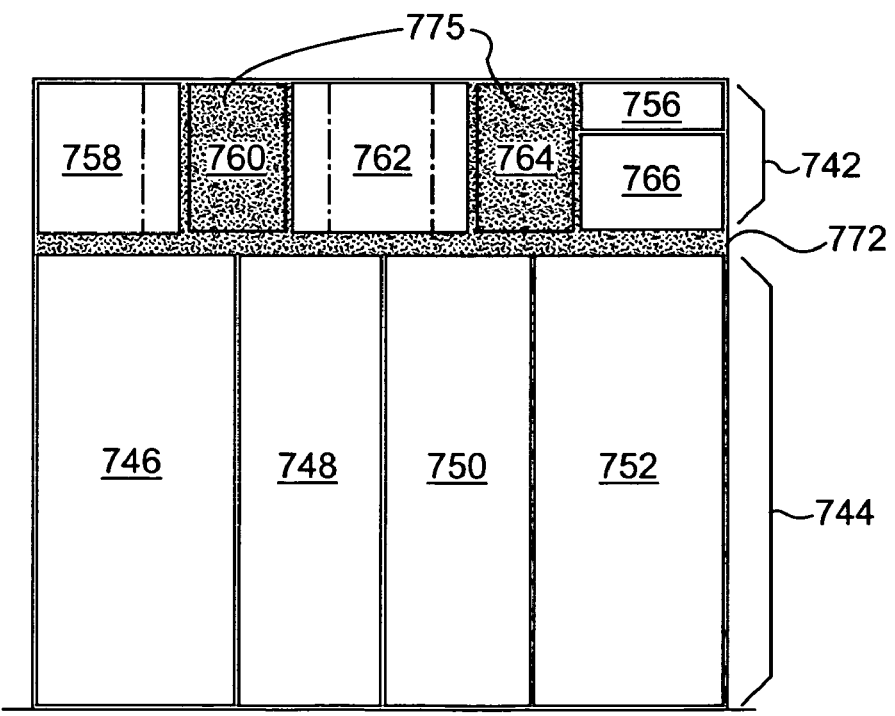
FIG. 20 is a top view of a distal portion of a test strip illustrating a plurality of electrical contacts forming a code according to an embodiment of the present invention.

One such code is illustrated in FIG. 20, where conductive contacting pads 760 and 764 are overprinted with an electrical insulting material, such as, for example, a non-conductive (insulating) ink layer 775. A non-conductive ink layer 775 significantly increases the impedance (and may even preventing the flow of electric current therealong) between the corresponding connector contacts (in this example, connector contacts 6 and 8) and the underlying strip portion at various predetermined contacting pads within the conductive region 742 of distal strip contact region 726. Just as described above, with regard to FIG. 18D, the use of non-conductive insulating ink 775 is particularly advantageous relative to other methods of altering the conductivity of a strip portion.

Depending on the arrangement of the electrical strip contacts, the discrete portions of electrical insulating material forming each layer 775 can be applied to the top side of the strip, the bottom side of the strip, or a combination of both.

Upon connection of the contacting pads 758, 760, 762, 764, and 766 in FIG. 6 to the corresponding connector contacts 740, the meter will read a particular code based on the number, and pattern, of contacting pads overprinted with a non-conductive ink layer 775. In other words, the use of non-conductive ink layer 775, provides a switching network to be read by the meter. When an insulator is printed over one of the conductive surfaces of contacting pads 758, 760, 762, 764, and 766, it prevents the flow of electric current therealong and alters the conductive path between the contacting pad and connector contact (e.g. where no current flows). When no insulator is printed over the conductor current flow is relatively unimpeded (a low impedance path).

Upon reading a particular code, an internal memory within the meter can access, through a stored microprocessor algorithm, specific calibration information (such as, for example, calibration coefficients) relating to the particular test strip. The meter can read the code through either an analog or digital method. In the analog mode, a preset resistive ladder is interconnected within the meter to the second plurality of connector contacts 740 (labeled 5-9 in FIG. 19) such that permutations of printed non-conductive ink can be correlated to a distinct lot code using a voltage drop, resistance, or current measurement. The analog method also can be simultaneously used as the auto-on/wake-up feature as long as each code has at least one pad free of non-conductive ink that can make a low impedance connection to wake the meter up by closing an open circuit. The analog voltage, resistance, or current level could be used to signal the meter to access any of the data referenced above particular to the underlying test strip.

Figure 21:
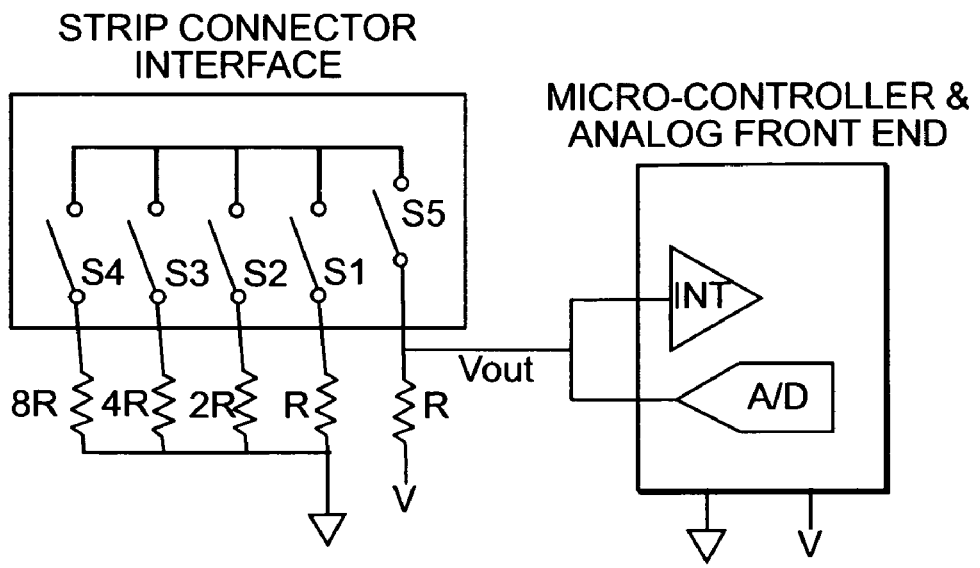
FIG. 21 is a simplified schematic diagram of the electrical connections between a meter and a plurality of electrical contacts of a test strip according to an embodiment of the invention according to an embodiment of the present invention.

FIG. 21 depicts a schematic diagram of the electrical connections between a meter and contacting pads 758, 760, 762, 764, and 766 of a test strip according to an embodiment of the invention. Switch S5 of FIG. 21 provides the connection to a single voltage source V. Accordingly, switch S5, represents the required connection of contacting pad 766 and connector contact 9 in the analog code reading process. Switches S4-S1 schematically represent the connection between connector contacts 5-8 and contacting pads 758-764 of FIG. 19, respectively. When a non-conductive ink layer 775 is provided over one of the contacting pads 758, 760, 762, and 764, the corresponding switch, S4, S3, S2, or S1, will prevent the flow of electric current therealong upon physical engagement with a corresponding connector contacts 5-8. Accordingly, a particular code will correspond to a particular switching configuration, in the switch network of FIG. 21.

As further seen in FIG. 21, each of switches S4-S1 close to add a distinct value of additional impedance to the closed circuit, by bridging the connection to a particular resistor. Therefore, through the application of Ohm's and Kirchhoff's laws, a circuit measurement at $V_{out}$ will provide distinct values based on the particular code presented by test strip 710. In an alternative embodiment, the direction of current flow can be reversed, if desired, by connecting switch S5 to common ground and instead connecting the resistor R to the single voltage source.

Figure 22:
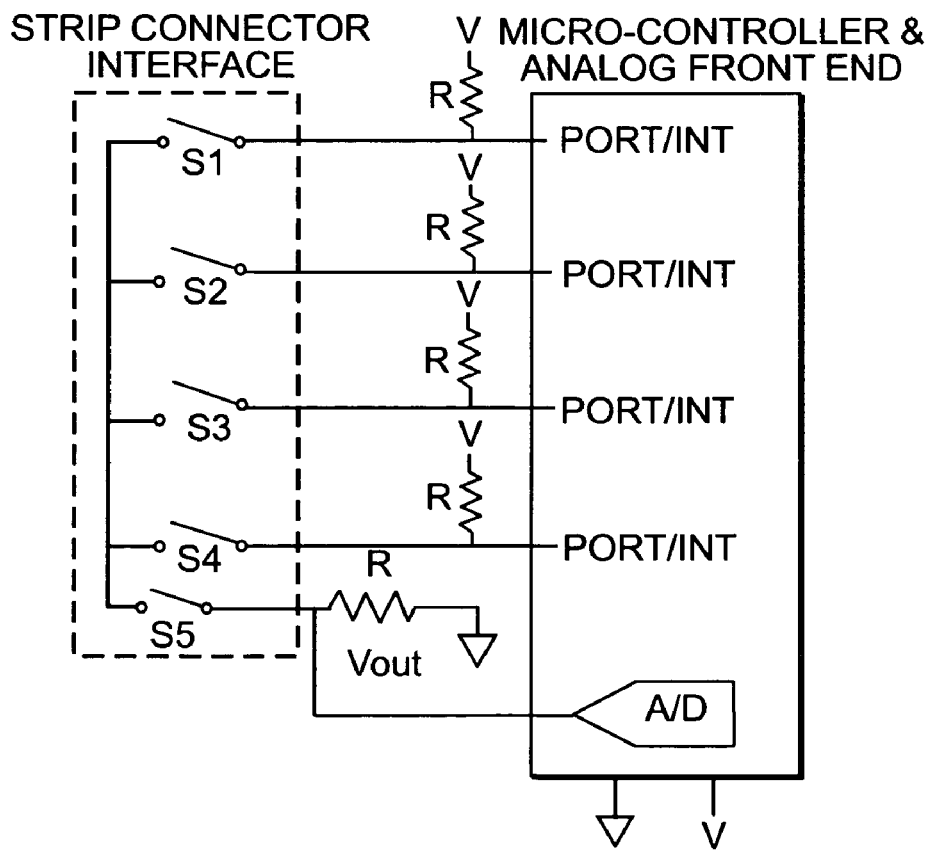
FIG. 22 is an alternative simplified schematic diagram of the electrical connections between a meter and a plurality of electrical contacts of a test strip according to an embodiment of the invention.

In the digital mode, as schematically represented in FIG. 22, each contacting pad 758-766, would be read as an individual input, unlike the single input used by the analog method. For the digital method to be simultaneously used as an auto-on/wake-up feature, the inputs would need to be wire-orred together or connected to an interrupt controller of a micro-controller. Each code must have at least one pad free of non-conductive ink 775 such that a low impedance connection can be made to wake-up the meter's micro-controller.

Non-conductive ink 775 with levels of high and low impedance produce a binary code yielding a code index based on the number of pads (P) implemented, where the number of codes is $N=2^P$. It is possible, however, for a code to comprise an arrangement where none of the electrical strip contacts are covered with electrical insulating material (a code will all logical "1"s, i.e. all conductors). The number of codes possible when integrated with an auto-on/wake-up feature, however, is reduced to $N=2^P-1$. In a system having an auto-on/wake-up feature, a code with all zeros (all insulators) is not an active code as it will not wake up the meter.

When a strip 710 is inserted into the meter connector portion 730, one contact is closed and wakes up the meter by pulling the microcontroller's interrupt either high or low. The meter will then check the voltage out ($V_{out}$) to determine the test type and then read the code bits (S1,S2,S3,S4) to determine the code value. The code value selected can, for example, be associated with a stored set of coefficients in the meter's memory for use in a glucose mapping algorithm that is particularly correlated to the reagent applied to the measuring electrode region. This code can also be associated with other types of strip parameter information, such as those referenced above. It could also select different meter configuration options as well. The voltage drop across the series resistor R at Vout in FIG. 22 can be sensed, to determine if code vales are within a predetermined range for use as a confirmation signal. This can also be used to determine strip identification (check strip, manufacturing probe, and different test type).

In addition to providing either a high or low impedance level (through the application or absence of an insulating layer of non-conductive ink 775 over one of the contacting pads) a particular resistive element may be applied over a particular contacting pad. The resistive element introduces an increased level of impedance into a circuit that reduces (but does not necessarily prevent) the flow of electric current. Accordingly, the use of a specific resistive element over a particular contacting pad provides an intermediate level of resistance directly on the contacting pad of the test strip. When this intermediate level of resistance is connected to the meter through engagement with a corresponding meter connector contact, the meter can detect this "intermediate" level (e.g. through a circuit measurement of voltage drop by applying Ohm's and Kirchhoff's laws).

The detection of such an intermediate level can be used by the meter's processor to access an entire new set of code data relating to the particular test strip. In other words, providing a resistive element coating can be used to expand the number of codes available with a set number of contacting pads. For example, a strip may be formed with a particular code through a particular pattern of non-conducting insulating ink 775. When one of the conducting contacting pads is formed to include a particular resistive element, that same code represented by the pattern of non-conducting ink 775 now can be read by the meter to access an entirely different set of data. As an example, the contacting pad 766 of FIG. 20 (or any of the available contacting pads) could be formed to include a resistive element. As a non-limiting example, the resistive element could be provided in the form of a printed conductive ink. The thickness of the printed ink forming the resistive element, and resistivity of the ink composition, can be varied to achieve the desired resistance for a particular contacting pad. The additional information made available through this expansion of codes can include, but is not limited to, information related to hematocrit correction, information related to meter upgrades, and information related to the particular strip type. Accordingly, the use of such a resistive element can be used to expand the number of code configurations available with a set number of contacting pads.

It should be noted that the particular disclosed configurations of test strip 710, and in particular the configuration of connector contacts 738, 740 and the corresponding first and second plurality of electrical strip contacts, are merely exemplary, and different configurations could be formed without departing from the scope of the invention. For example, the underside of strip 710 can be formed to incorporate an additional number of contacting pads in order to increase the size (and thereby the amount of information) in the code index. The additional contacting pads on the underside of strip 710 could represent a third plurality of electrical strip contacts, thereby increasing the number of codes available. The number of available codes could thereby be expanded by applying an insulating coating to particular pads on the underside of strip 710 in addition to the coating of pads on the opposite side of the strip.

While the foregoing disclosure provides an example of a code formed through a pattern of non-conductive ink and/or resistive elements on the test strip, alternative on-strip coding arrangements are contemplated. The alternative code arrangements include, but are not limited to, a code formed by a pattern of circuit elements on the test strip that alter the capacitance or inductance of a circuit, a bar-code pattern representing the code readable by the controller, a colored pattern representing the code readable by the controller, a code based on the relative transmission/reflection (e.g. opacity) of an element on the test strip, a code based on the relative florescence or luminescence (including electro-luminescence) of an element on the test strip, a code based on a particular electrochemical property of an element on the test strip, a code based on a particular PH level of an element on the test strip, a code based on the particular spatial distribution of elements on the test strip, a code based on magnetic particles provided on the test strip (e.g. a magnetic stripe such as those provided on credit/ATM cards), a code based on a particular radio frequency signal emitted from an element on the test strip (e.g. passive resonators such as those used in anti-theft tags to prevent shoplifting), and a code based on a particular pattern of optical characters on the test strip readable through optical character recognition by the controller.

Regarding the above examples, a portion of the test strip can be provided with a particular element that can be detected by the meter upon insertion of the test strip into the meter interface. For example, regarding the color pattern example, the meter could be equipped with a photo-detector element that detects the particular color. Based on the particular detected color, the meter then accesses specific data corresponding to the particular test strip readable by the controller.

3b. Separate Coding Device Examples

Figure 14:
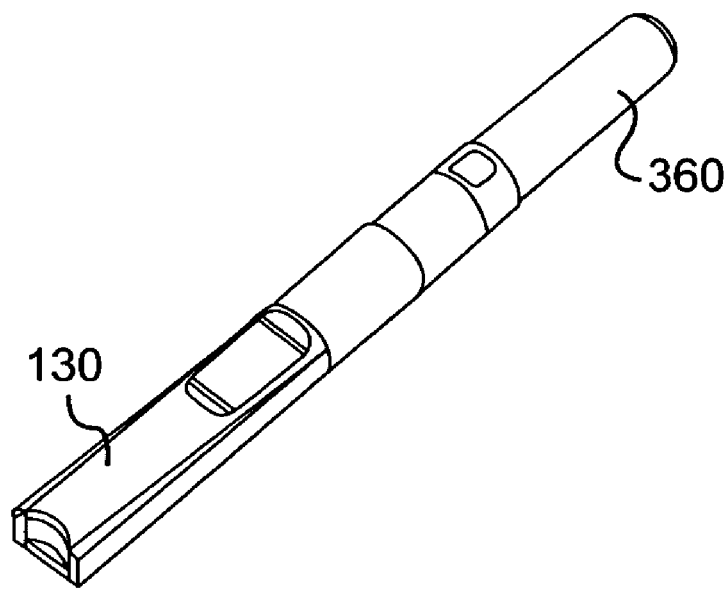
FIG. 14 is a perspective view of a lancing device with a replaceable meter.
Figure 14:
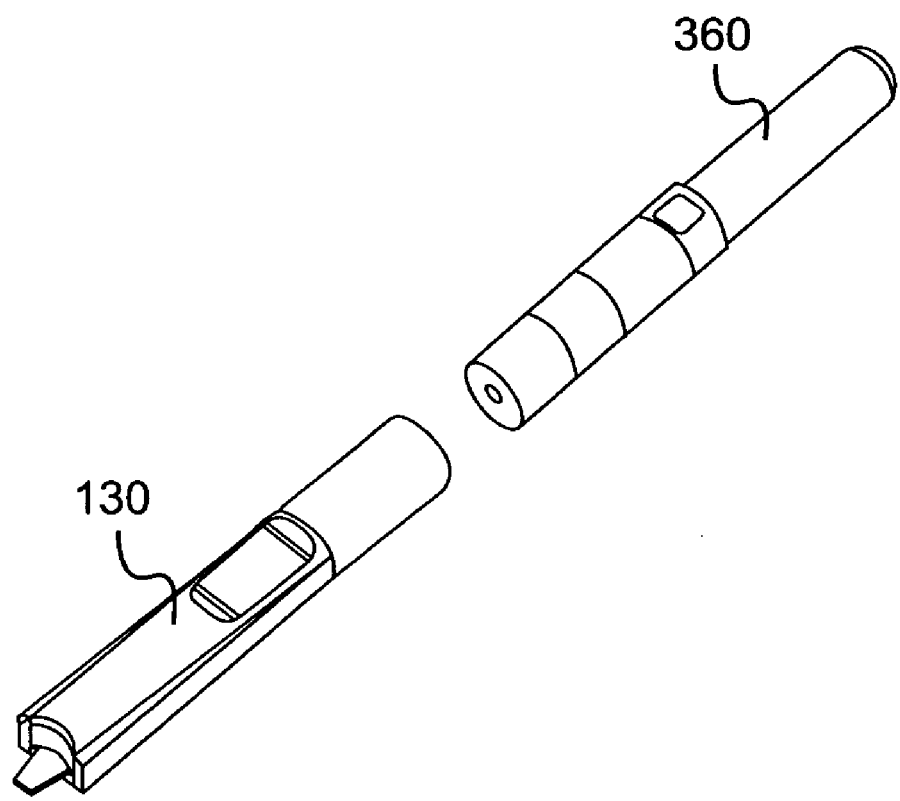
Figure 23:
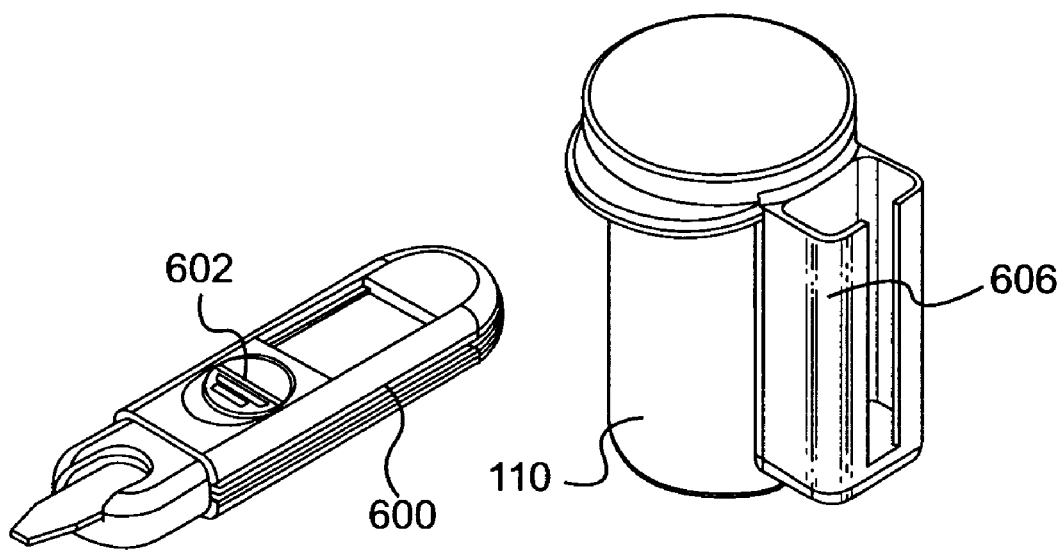
FIG. 23 is a perspective view of a remote meter with on-strip coding and a strip ejector mechanism.
Figure 24:
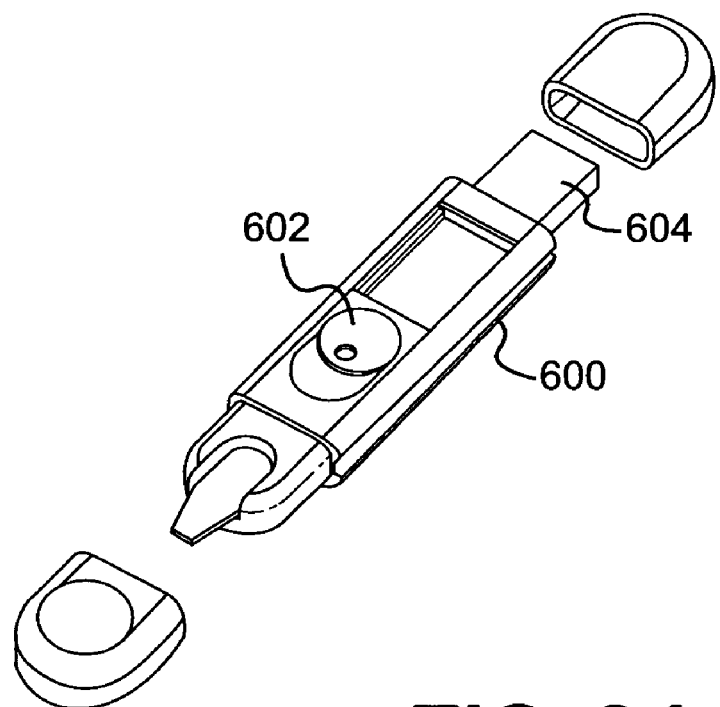
FIG. 24 is a perspective view of a remote meter USB data connecter with on-strip coding and a strip ejector mechanism.

As illustrated in FIGS. 23 and 24, the reduced size of the previously described test strips 120 and/or 710 may require a meter 130 with a strip ejector mechanism 602 in order to dispose of the strip 120 without touching it. Moreover, a lancing device 360 may be integrated with the meter 130 as shown in FIG. 14.

Another coding method that allows the metering device 130 to be removed from the test strip container 110 and transferred to another container is button coding. A user selects a code number on the meter 130 each time the meter 130 is interconnected to a different container. The user then enters a code that is visually read by the user based on a value printed on the test strip container 110. At least one advantage of using button coding is that it does not require a secondary manufacturing operation to add a code to a test strip 120 after the code is determined for that strip lot. However, this coding method may be less desirable than universal and on-strip coding due to the possibility of coding entry errors by the user.

In an alternative embodiment, code chip coding may also be used as an effective means for calibrating the meter 130. The method of code chip coding requires the user to insert a code chip with lot specific information included in each package of strips 120 into the meter 130. Code chip coding is advantageous in that it provides a means for data storage. However, there is a possibility that the user could confuse old code chips for new ones by mistake, thus causing coding errors. Also, it is also not always space efficient to use code chips due to package and connector size. Moreover, code chip coding requires the user to handle an additional system component for testing than other coding techniques. Nevertheless, code chip coding is a viable coding alternative.

Figure 25:
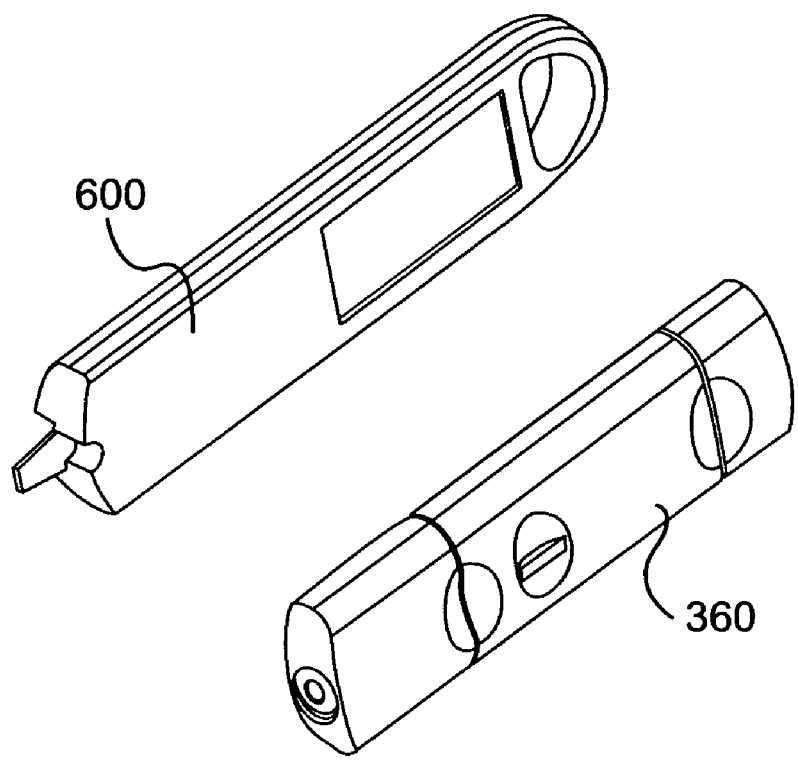
FIG. 25 is a perspective view of a remote meter with on-strip coding and a strip ejector mechanism attached to a lancing device.
Figure 25:
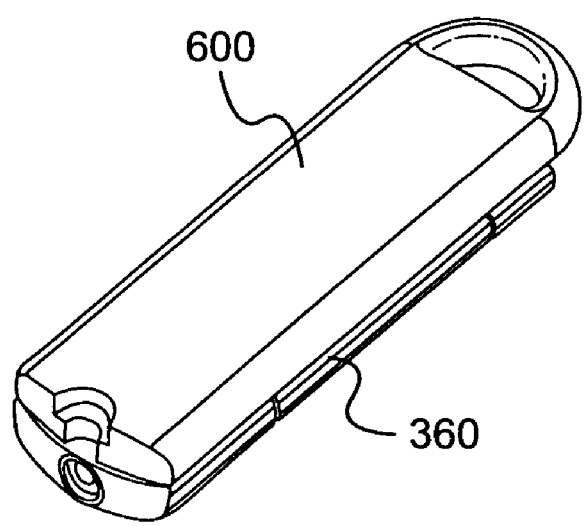
Figure 26:
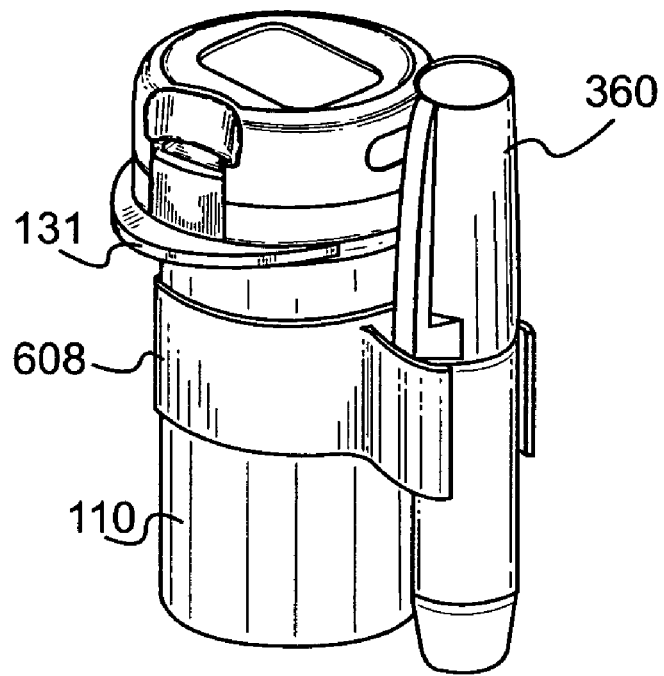
FIG. 26 is a perspective view of a holder in the form of a clip placed around a container.
Figure 26:
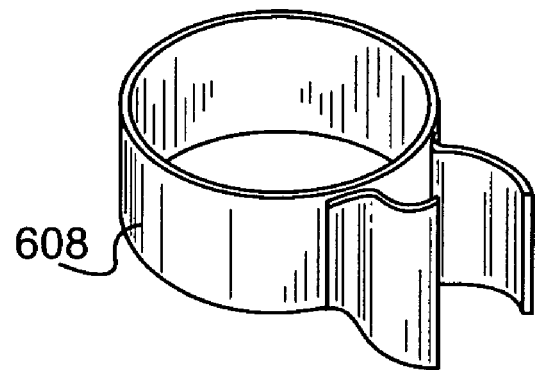
Figure 27:
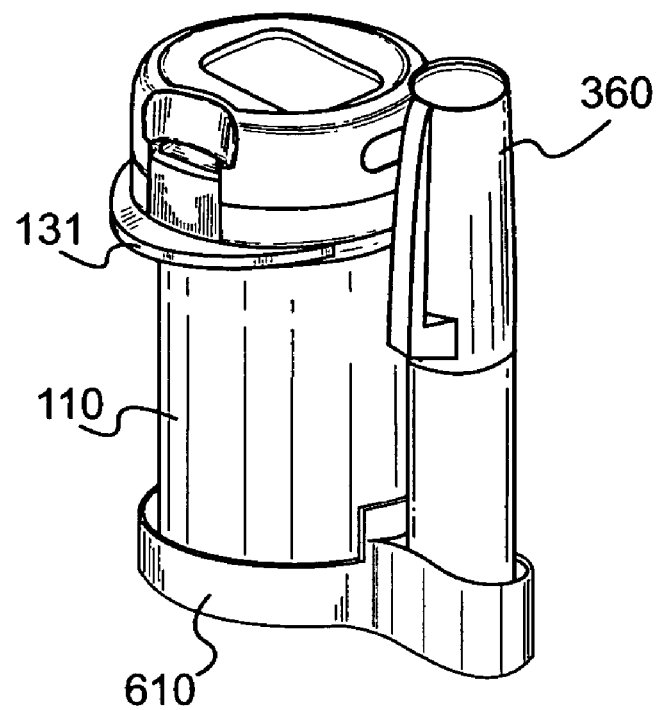
FIG. 27 is a perspective view of a holder in the form of holes used to contain a container and a lancing device.
Figure 27:
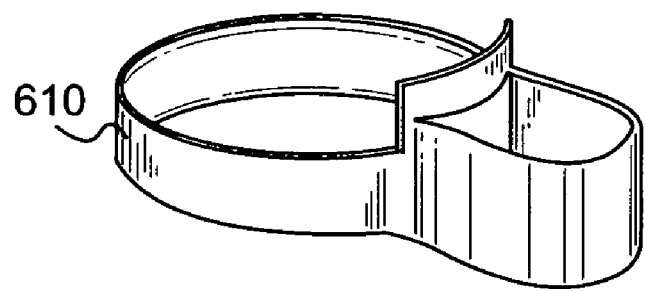

Alternatively, meter 130 may be calibrated by means of a Universal Serial Bus (USB) device 600. Each test media container 110 (or a co-packaged group of containers from the same lot) may be provided with a data storage device 600 that stores the calibration data electronically. To calibrate the meter 130 for the test media in the particular container 110 or package, the user simply plugs the corresponding data storage device 600 into a connector (not shown) on meter 130. The controller 400 then obtains the necessary instructions 402 or data from the data storage device 600. In addition, USB remote meters 600 can transfer data to a personal computer (PC) (not shown) directly from the integral USB data connector 604 (e.g., as set forth in commonly-assigned application Ser. No. 11/118,494 filed May 2, 2005, which is incorporated herein by reference in its entirety). The data connector 604 can also be attached to test strip container 110 via a holster-type receptacle 606 formed on the side of the test strip container 110 (as shown in FIG. 23), providing a convenient form to transfer data directly to the PC. Moreover, this device can be used as an "electronic log book" to transfer stored data in the meter 130 to the PC. The display shows basic results, but date and time can be set via PC and time and date information sent to the PC with each result. In addition, the PC application can be launched after detecting the USB connection to the PC. Alternative embodiments provide a remote meter 600 with on-strip coding and an ejector button 602 attached to a lancing device 360 that can be used together or separately as illustrated in FIGS. 23-25.

3c. Preventive Measure Examples

Although the coding methods described above are designed to prevent meter calibration errors, the integrated diagnostic test system further employs additional safeguards (in addition to the on-strip "coding" approach described in FIGS. 15-22) to minimize the chance that a user will mistakenly use meter 130 with test media from a brand or lot for which the meter 130 has not been calibrated.

Illustrative embodiments of the present invention provide one or more preventive measures that may disable one or more functions of the meter upon the occurrence of certain triggering events. For example, the preventive measure may render meter 130 wholly inoperative after the meter 130 has been used for a certain period of time or quantity of tests, or with a certain quantity of test media. The meter 130 may then be simply disposed of or returned to the manufacturer for remanufacturing. Alternatively, the preventive measure may render only the diagnostic testing function of controller 400 inoperative, or simply prevent the meter from displaying the result of a diagnostic test. The user may then retain meter 130 in order to use its remaining functions.

A given preventive measure may be triggered by the occurrence of a triggering event, such as the expiration of a certain time period. The time period may be related to particular test media, e.g., a particular container 110 or lot of test strips 120 for which meter 130 has been calibrated or otherwise associated. For example, a preventive measure may be triggered if the current date is after an expiration date of test media associated with the meter 130, e.g., where the manufacturer indicates that the particular test media should not be used more than two years after its date of manufacture. Alternatively, the expiration date may be determined relative to a date a particular container was opened, e.g., where the manufacturer indicates that the test media should not be used more than 2 months after its container 110 has first been opened.

The date a particular container 110 of test media has first been opened may be estimated or determined in a number of ways. For example, a detector 412 monitors the current draw of the LED 253 and relays the information to the meter 130, such that the meter 130 can ascertain when the vial 110 has been opened. This function need not be performed by a separate component, but may be performed by the controller 400. In addition, where meter 130 is precalibrated for use with a single container or lot of test strips, the date that the container has first been opened may be estimated by determining the date the meter was first turned on, e.g., by instructing controller 400 to save the date or start a timer when the meter 130 is first turned on or otherwise activated for use. However, because the user may turn on the meter (e.g., to familiarize themselves with the functions of the meter or to calibrate the meter) an indeterminate time before actually using the meter to conduct a diagnostic test, the date of first use of the meter can be estimated by instructing controller 400 to save the date or start a timer when meter 130 is first used to run a diagnostic test. Similarly, where meter 130 is calibrated by the user, the date a particular container is opened may be estimated by instructing controller 400 to save the date or start a timer when meter 130 is first used to conduct a diagnostic test after being calibrated or otherwise associated with a given plurality of test strips. Alternatively, where meter 130 is attached to a particular container 110, user control function 430 may include a switch actuated when the user opens the closure 140, e.g., so that the controller is informed when the container 110 is first opened. One having ordinary skill in the art will understand that other ways of determining first use of the container 110 are possible.

Moreover, an optical sensor, electrical measurement, mechanical switch or acoustic sensor can also be used to determine how long and the accumulated time the container 110 has been open. This information can be valuable in determining test strip 120 viability, or in the case of a humidity sensitive test strip 120, for example, if a test strip 120 can be recovered by placing it in a desiccated container 110 for a longer period of time.

In addition, when the container 110 of test media is opened, the meter 130 can automatically or selectively turn on the display 133. In other embodiments, controller 400 may be started or awakened from a sleep state when the container 110 is first opened.

Detector 412 may also monitor the current draw of the LED 253 and relay the information to the meter 130, such that the meter 130 can ascertain when the LED 253 has been illuminated. This function need not be performed by a separate component, but may be performed by the controller 400. Controller 400 is configured to start a timer upon determining that the light source 253 has been illuminated. Analogous to the method described above, the timer is designed to track an elapsed time from the first time a container 110 is opened by a user. In addition, the timer is also configured to signal the controller 400 to extinguish the light source 253 and alert the user after a predetermined time. The alert may be, for example, a visual, an audio, a kinetic, or a combination alarm.

The time period need not be related to a particular lot or container of test media. A particular preventive measure may be triggered a predetermined time after manufacture or first use of meter 130, or first use of a particular meter function (e.g., performance of a diagnostic test), without regard to any characteristic of the test media. For example, a given preventive measure may be triggered three months after first use of the meter to conduct a diagnostic test. In any case, indicator function 450 may be used to indicate the time remaining until preventive measures are triggered.

Alternatively or in addition, controller 400 may maintain a running count of the quantity of test media used or the quantity of diagnostic tests performed by the meter using the current calibration data. The quantity of test media used may be estimated by the number of times that test media have been inserted in media interface 410 or, preferably, the number of times a sample has been detected, e.g., by the media sensors. The running count may be compared to a quantity of tests or test media allowed before triggering of a preventive measure. The allowed quantity may relate to a quantity of test media that were originally packaged with meter 130 by the manufacturer or distributor, e.g., the quantity of test media originally contained in an associated container 110. As a further alternative, the allowed quantity may exceed the number of test strips contained in the associated packaging or container 110 by a small amount, e.g., 10%. If the running count exceeds the operative quantity, then a preventive measure may be triggered. Indicator function 450 may be used to indicate the quantity of diagnostic tests or test media remaining before a preventive measure is activated.

Information related to the trigger for the preventive measure (e.g., the allowed time period, the expiration date of the associated test media, the quantity of diagnostic tests, the quantity of diagnostic test strips, etc.) may be obtained in a manner similar to the calibration data. In an illustrative embodiment, controller 400 is distributed with the trigger information, e.g., encoded in memory 406 or elsewhere in controller 400. Alternatively, the trigger information may be entered by the user. For example, the trigger information may be appended to the calibration data that is entered or downloaded by the user. Alternatively, the user may enter or download the trigger information (or a code from which controller 400 may derive the trigger information) separately from the calibration data. As an additional example, trigger information may be "coded" directly onto the particular test medium along with the calibration data previously described with regard to the approach of FIGS. 15-22. For example, the coded information read by controller 400 from the test media could signal memory 406 to access the particular data corresponding to the specific code.

Controller 400 may be instructed to periodically determine whether a particular preventive measure is triggered. For example, controller 400 may determine whether a preventive measure is triggered on a daily or weekly basis. Alternatively or in addition, controller 400 may be instructed to determine whether a given preventive measure is triggered whenever a certain event occurs. For example, controller 400 may be instructed to determine whether a preventive measure is triggered whenever a test strip 120 is inserted into test strip interface 110, whenever a sample is detected by the media sensors, whenever a diagnostic test is performed by the controller, whenever the result of a diagnostic test is displayed, or whenever a certain user control 430 or other function of meter 130 is actuated, etc.

The preventive measures may take a number of forms. Where the power source 420 of the meter is finite (e.g., a battery), the preventive measure may manipulate the life of power source 420 so that the power source, e.g., a battery within housing 131, becomes inoperative soon after the preventive measure is triggered. For instance, controller 400 may increase the load on the power source when the preventive measure is triggered. The load may be increased, e.g., by raising the frequency of system clock 408 so that the rate power is consumed by the controller 400 and other electronic functions is increased. The power source 420, and thus meter 130, will then become inoperative in a relatively short period of time. Alternatively or in addition, controller 400 may be instructed to cause the meter 130 to remain in an "on" state once the preventive measure is triggered, thus draining the power source. As a further alternative, controller may be instructed to open a switch or blow a fuse so as to disconnect power source 420 from the electronic functions of the meter 130. For this embodiment, meter housing 131 may be constructed so that power source 420 is not replaceable. Indicator function 450 may indicate an estimation of the time remaining before the power source 420, and thus the meter 130, become inoperable.

Another preventive measure may prevent a diagnostic test from being performed. For example, where meter 130 includes an auto-on function for initiating a diagnostic test upon insertion of a test strip 120 into interface 410 (e.g., as set forth in U.S. Pat. Nos. 6,743,635 and 6,946,299, incorporated by reference above), controller 400 may be instructed to disable the auto-on function when the preventive measure is triggered. Controller 400 may nevertheless allow the user to turn on the meter using user control function 430 so as to allow access to other functions of the meter. For instance, controller 400 may allow the user to turn on the meter and review previous test results and/or associated voice messages stored in memory 406.

As another alternative, the preventive measure may allow the a diagnostic test to be performed, but prevent the indicator function from indicating the result. Instead, the meter may display a message indicating that the meter is not calibrated and/or that the meter needs to be replaced. As before, controller 400 may still allow the user to review previous test results and any associated voice messages stored in memory 406. The meter 130 itself may then be given or sent to the user's medical care provider. The medical care provider may then review the results of the diagnostic tests and/or associated voice messages for use in treating the user.

As a further preventive measure, controller 400 may be instructed to reconfigure the function of meter 130. For instance, controller 400 may instructed to reconfigure indicator function 450 to indicate other information in place of a result of a diagnostic test. For example, the indicator function 450 may be reconfigured to indicate the time and/or the date. Alternatively, indicator function 450 may be reconfigured to indicate readings from environmental sensors 480. For example, the meter 130 may indicate the temperature and/or humidity, together with the appropriate units, on display 133. As another alternative, controller 400 may be instructed to reconfigure the voice message function 470 to allow voice messages to be recorded for purposes other than indicating results of a diagnostic test.

The user control function 430 may be reconfigured in accordance with the reconfiguration of the indicator function. For example, the indicator function 450 may be reconfigured to act as a timer, e.g., a kitchen timer. User control 430 may be correspondingly reconfigured to control the timer. For example, user control 430 may be reconfigured to start and stop the timer. Alternatively, user control 430 may be reconfigured to switch between or adjust displays of the time, date, temperature and/or humidity.

The meter may be provided with a fastener (e.g., a magnet, a VELCRO hook and loop fastener, an adhesive, etc.) on its back so as to allow the user to place the meter 130 where its new function will be useful. For example, the user may place the meter on their refrigerator. In this manner, the user may be reminded of the meter manufacturer's or distributor's name and/or logo (which may be placed next to the display 133) in a context outside of the use of the meter 130 for diagnostic testing.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for diagnostic testing, the system comprising:
    a meter for performing a diagnostic test on a sample applied to test media, the meter comprising:
        a housing;
        an interface for accepting test media in order to perform the diagnostic test; and
        a controller configured to perform the diagnostic test; and
    a container operatively associated with the meter, the container having an opening to a continuously connected interior volume permitting contact between a plurality of loose, singulated test media compatible with the meter,
    wherein the test media include at least one test strip embedded with a code readable by the controller to identify data particular to the test strip, and
    wherein the meter housing is positioned atop the container and a bottom surface of the housing is configured to engage the container and selectively unseal and reseal the opening to the interior volume of the container.

2. The system of claim 1, further comprising a light source positioned to illuminate an interior of the container.

3. The system of claim 1, wherein the at least one test strip includes a conductive pattern including electrical contacts disposed at a distal region of the strip forming a distinct pattern representing the code readable by the controller to identify data particular to the test strip.

4. The system of claim 1, wherein the at least one test strip includes a code pattern representing the code readable by the controller to identify data particular to the test strip.

5. The system of claim 1, wherein the at least one test strip includes a colored pattern representing the code readable by the controller to identify data particular to the test strip.

6. The system of claim 3, wherein the at least one test strip comprises:
   at least one electrically insulating layer upon which the conductive pattern is formed; and
   wherein each of the electrical contacts is selectively coverable with a discrete portion of electrical insulating material to produce a binary code based on the number of electrical contacts, the resulting binary code representing the code readable by the controller to identify data particular to the test strip.

7. The system of claim 3, wherein the electrical contacts are configured for contact, when inserted into the meter interface, with a plurality of contacts within the meter interface.

8. The system of claim 7, wherein at least one of the electrical strip contacts include a resistive element disposed thereon to form part of the distinct pattern readable by the meter upon insertion of the test strip into the meter interface.

9. The system of claim 1, wherein the code is utilized by the meter to access particular calibration parameters stored therein related to the particular test strip.

10. The system of claim 1, wherein the code is utilized by the meter to perform a particular measurement corresponding to the particular type of test strip.

11. The system of claim 1, wherein the code is utilized by the meter to access particular calibration parameters stored therein related to an entire particular test strip lot.

12. The system of claim 1, wherein the container comprises a holder configured to receive one or more devices used for diagnostic testing, and wherein the opening is accessible to a user of the system.

13. The system of claim 12, wherein the holder engages the meter.

14. The system of claim 12, wherein the holder engages a lancet.

15. A system for diagnostic testing, the system comprising:
   a meter for performing a diagnostic test on a sample applied to test media, the meter comprising:
      a housing;
      an interface for accepting test media in order to perform the diagnostic test; and
      a controller configured to perform the diagnostic test; and
   a container operatively associated with the meter, the container having an opening to a continuously connected interior volume permitting contact between a plurality of loose, singulated test media compatible with the meter housed therein,
   wherein the meter housing is positioned atop the container and a bottom surface of the housing is configured to engage the container and selectively unseal and reseal the opening to the interior volume of the container, and
   wherein the test media include at least one diagnostic test strip comprising:
      at least one electrically insulating layer;
      a conductive pattern formed on the at least one insulating layer including at least one electrode disposed on the at least one insulating layer at a proximal region of the strip, electrical strip contacts disposed on at least one insulating layer at a distal region of the strip, and conductive traces electrically connecting the at least one electrode to at least some of the electrical strip contacts; and
      a reagent layer contacting at least a portion of the at least one electrode,
      wherein each of the electrical strip contacts is selectively coverable with a discrete portion of electrical insulating material to at least partially form a distinct pattern readable by the controller to identify data particular to the test strip.

16. The system of claim 15, wherein the at least one test strip includes a bar-code pattern representing the code readable by the controller to identify data particular to the test strip.

17. The system of claim 15, wherein the at least one test strip includes a colored pattern representing the code readable by the controller to identify data particular to the test strip.

18. The system of claim 15, further comprising at least one discrete portion of electrical insulating material disposed over at least one of the electrical strip contacts to at least partially form a distinct pattern readable by the controller to identify data particular to the test strip.

19. The system of claim 15, wherein the distinct pattern readable to identify data particular to the test strip comprises an arrangement where none of the electrical strip contacts are covered with electrical insulating material.

20. The system of claim 18, wherein a resistive element is disposed over at least one of the electrical strip contacts to form part of the distinct pattern readable to identify data particular to the test strip.

21. The system of claim 15, wherein each of the at least one electrodes is individually connected to one contact in a first plurality of electrical strip contacts.

22. The system of claim 21, wherein the conductive pattern at the distal region of the strip includes a second plurality of electrical strip contacts.

23. The system of claim 22, wherein the first and second plurality of electrical strip contacts are positioned to form distinct groups of electrical contacts, the groups being spaced from one another.

24. The system of claim 22, wherein the second plurality of electrical strip contacts form a discrete set of contacting pads.

25. The system of claim 18, wherein the insulating material comprises a non-conductive insulating ink.

26. The system of claim 24, wherein the contacting pads are configured for contact, when inserted into a compatible meter, with a plurality of contacts in a corresponding connector of the meter.

27. A system for diagnostic testing, the system comprising:
   a meter for performing a diagnostic test on a sample applied to test media, the meter comprising:
      a housing;
      an interface for accepting test media in order to perform the diagnostic test; and
      a controller configured to perform the diagnostic test; and
   a container operatively associated with the meter, the container having an opening to a continuously connected interior volume permitting contact between a plurality of loose, singulated test media compatible with the meter housed therein,
   wherein the meter housing is positioned atop the container and a bottom surface of the housing is configured to engage the container and selectively unseal and reseal the opening to the interior volume of the container, and
   wherein the test media include at least one diagnostic test strip comprising:

at least one electrically insulating layer;

a conductive pattern formed on the at least one insulating layer including at least one electrode disposed on the at least one insulating layer at a proximal region of the strip, electrical strip contacts disposed on at least one insulating layer at a distal region of the strip, and conductive traces electrically connecting the electrodes to at least some of the electrical strip contacts;

a reagent layer contacting at least a portion of at least one electrode;

a first plurality of electrical strip contacts comprised of contacts individually connected to an electrode; and a second plurality of electrical strip contacts comprised of the conductive pattern at the distal region of the strip, wherein an electrically insulating material separates the first and second plurality of electrical strip contacts.

28. The system of claim 27, wherein each of the electrical strip contacts comprising the second plurality is selectively coverable with a discrete portion of electrical insulating material to at least partially form a distinct pattern readable by the controller to identify data particular to the test strip.

29. The system of claim 28, further comprising at least one discrete portion of electrical insulating material disposed over at least one of the electrical strip contacts to at least partially form a distinct pattern readable to identify data particular to the test strip.

30. The system of claim 28, wherein the distinct pattern readable to identify data particular to the test strip comprises an arrangement where none of the electrical strip contacts are covered with electrical insulating material.

31. The system of claim 29, wherein a resistive element is disposed over at least one of the electrical strip contacts to form part of the distinct pattern readable to identify data particular to the test strip.

32. The system of claim 27, wherein the second plurality of electrical strip contacts form a discrete set of contacting pads.

33. The system of claim 27, wherein the insulating material comprises a non-conductive insulating ink.

* * * * *